(12) United States Patent
Schadt et al.

(10) Patent No.: US 7,960,413 B2
(45) Date of Patent: *Jun. 14, 2011

(54) PYRAZOLE COMPOUNDS

(75) Inventors: Oliver Schadt, Rodenbach (DE); Kai Schiemann, Seeheim-Jugenheim (DE); Christoph Van Amsterdam, Darmstadt (DE); Gerd Bartoszyk, Weiterstadt (DE); Christoph Seyfried, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 322 days.

This patent is subject to a terminal disclaimer.

(21) Appl. No.: 10/551,905

(22) PCT Filed: Mar. 8, 2004

(86) PCT No.: PCT/EP2004/002352
§ 371 (c)(1),
(2), (4) Date: Oct. 5, 2005

(87) PCT Pub. No.: WO2004/089888
PCT Pub. Date: Oct. 21, 2004

(65) Prior Publication Data
US 2006/0276650 A1 Dec. 7, 2006

(30) Foreign Application Priority Data
Apr. 5, 2003 (DE) .................................. 103 15 571

(51) Int. Cl.
*A61K 31/44* (2006.01)
*A61K 31/40* (2006.01)
*C07D 401/00* (2006.01)
*C07D 231/10* (2006.01)
*C07D 231/12* (2006.01)

(52) U.S. Cl. .................. 514/341; 514/429; 546/275.4; 548/377.1

(58) Field of Classification Search .................. None
See application file for complete search history.

(56) References Cited

U.S. PATENT DOCUMENTS

| | | | |
|---|---|---|---|
| 3,926,999 A | 12/1975 | Poetsch | |
| 4,146,721 A | 3/1979 | Rainer | |
| 4,258,047 A | 3/1981 | Gante et al. | |
| 4,325,962 A * | 4/1982 | Rainer | 514/406 |
| 4,631,343 A | 12/1986 | Beck | |
| 6,043,261 A | 3/2000 | Hansen, Jr. et al. | |
| 6,100,259 A | 8/2000 | Xiang et al. | |
| 6,150,393 A | 11/2000 | Behan et al. | |
| 6,407,238 B1 | 6/2002 | Baron et al. | |
| 7,067,507 B2 | 6/2006 | Pulley et al. | |
| 7,368,578 B2 | 5/2008 | Momose et al. | |
| 2001/0044445 A1 | 11/2001 | Bamaung et al. | |
| 2002/0091116 A1* | 7/2002 | Zhu et al. | 514/211.15 |
| 2004/0034083 A1 | 2/2004 | Stephenson et al. | |
| 2005/0239797 A1 | 10/2005 | Gaster et al. | |
| 2006/0264419 A1* | 11/2006 | Schiemann et al. | 514/218 |
| 2006/0276650 A1 | 12/2006 | Schadt et al. | |
| 2007/0010531 A1* | 1/2007 | Schadt et al. | 514/255.05 |
| 2007/0093492 A1 | 4/2007 | Jiaang et al. | |
| 2007/0105871 A1 | 5/2007 | Schiemann et al. | |

FOREIGN PATENT DOCUMENTS

| | | |
|---|---|---|
| DE | 2141125 A | 2/1972 |
| DE | 2201889 | 7/1973 |
| DE | 2258033 | 5/1974 |
| DE | 2906252 | 8/1980 |
| WO | WO 96/33175 A | 10/1996 |
| WO | WO9831227 * | 7/1998 |
| WO | WO 9831227 | 7/1998 |
| WO | WO 01/29008 A | 4/2001 |
| WO | WO 0132626 | 5/2001 |
| WO | WO 0132627 | 10/2001 |
| WO | WO03031345 * | 4/2003 |
| WO | WO 03031435 | 4/2003 |
| WO | WO 03088958 | 10/2003 |
| WO | WO 03/099793 A | 12/2003 |
| WO | WO 2004/024705 A | 3/2004 |
| WO | WO 2004/024705 | 5/2004 |
| WO | WO 2004/037248 A | 5/2004 |

OTHER PUBLICATIONS

Vippagunta et al. Advanced Drug Delievery Reviews, 2001, 48, 3-26.*
Ross et al. Expert Opinion on Therapeutic Patents, 2003, 13(10), 1491-99.*
"Combat", http://www.aolsvc.merriam-webster.aol.com/dictionary/combating, accessed Nov. 20, 2009.*
Portnoy. Journal of Heterocyclic Chemistry, 1969, 6(2), 223-8, STN record.*
Database Beilstein 'Online! Beilstein Institute for Organic Chemistry, Frankfurt-Main, DE; Jun. 27, 1988, XP002283830.
Database Beilstein 'Online! Beilstein Institute for Organic Chemistry, Frankfurt-Main, Jun. 27, 1988, XP002283830.
Vippagunta et al. Advanced Drug Delivery Reviews, 2001, 48, 3-26.
"Premenstrual syndrome—Womens health and Medical Information in Medicinenet.com", http://www.medicinenet.com/premenstrual_syndrome/page5.htm, accessed Sep. 19, 2007.
"Amyotrophic Lateral sclerosis information page: National Institute of Neurological Disorders and Stroke (NINDS)", http://www.ninds.gov/disorders/amyotrophiclateralsclerosis/amyotrophiclateralsclerosis.htm, accessed Sep. 19, 2007.

(Continued)

*Primary Examiner* — Noble Jarrell
(74) *Attorney, Agent, or Firm* — Millen, White, Zelano & Branigan, P.C.

(57) ABSTRACT

Compounds of the formula (I) and salts and solvates thereof, in which X, $R^1$, $R^2$, $R^3$, $R^4$, $R^5$ and $R^6$ have the meanings indicated in Claim 1, are suitable as ligands of 5 HT receptors.

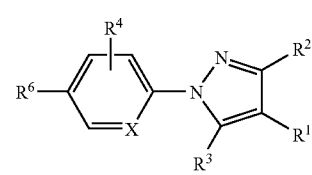

(I)

20 Claims, No Drawings

OTHER PUBLICATIONS

"Obsessive-compulsive behaviors and disorders: symptoms, treatment, and support", http://www.helpguide.org/mental/obsessive_compulsive_disorder_ocd.htm, accessed Sep. 19, 2007.

Journal of Clinical Psychiatry, 1999, 60, 1-8.

Crow, S. Expert Opinion on Investigational Drugs, 1997, 6(4), 427-36.

Ross et al., Expert Opinion on Therapeutic Patents, 2003, 13(10), 1491-99.

Takehito Ochi et al.: "FR143166 Attenuates Spinal Pain Transmission Through Activation of the Serotonig System" European Journal of Pharmacology, Bd. 452, 2002, pp. 319-324, XP002284473, The Entire Document.

Yoshiko Suzuki et al: "In Vitro and In Vivo Pharmacological Profile of 4-(4-Fluorobenzylidene)-1-{2-'5-(4-Fluorop Henyl)-1H-Pyrazol-4-Yl!Ethyl} Piperidine (NRA0161)" Life Sciences, Bd. 71, 2002, pp. 2603-2615, XP002284474, The Entire Document.

Katritzky et al: "1,3-Dipolar Cycloadditions of Electron-Rich Benzotriazol-1-Ylpropenes" J. Heterocyclic Chem., Bd. 33, 1996, pp. 1637-1646, XP002284475, Figure 28, pp. 1640.

Perez et al: "An Easy Method for the N-Alkylation of Amides, Carbamates, Ureas and Azoles . . ." Heterocycles, Bd. 60, Nr. 1, Nov. 25, 2002, pp. 167-175, XP002284476, Figures 10,11 and 12, pp. 168 and 173.

Database Chemabs 'Online! Chemical Abstracts Service, Columbus, Ohio, US; 1960, Grandberg, I.I. et al: "Pyrazoles. XII. Hydroxy-and Chloromethylation of 1-Substituted Pyrazoles" XP002284480, Found in STN, Database Accession No. 1961:99421, Summary & Zhurnal Obshchei Khimii, 30, 3324-8; CODEN: ZOKHA4; ISSN: 0044-460X, 1960.

Database Beilstein; Beilstein Institute for Organic Chemistry, Frankfurt-Main, DE; Nov. 29, 1988; XP002284481, Database Accession No. BRN 1127514 CAS-RN; 35000-58-9/ Summary & Dorn et al: J. Prakt. Chem., Bd. 313, 1971, pp. 236-246.

Bebernitz et al.: "The Effect of 1,3-Diaryl-'1H!-Pyrazol-4-Acetamides on Glucose Utilization in OB/OB Mice" J. Med. Chem., Bd. 44, Nr. 16, 2001, pp. 2601-2611, XP002284478; Schema 1, Methode A, Strukturen 2-5, Reaktionen A and B.

Echevarria et al: Research in the Azole Series. 102 '1!. Synthesis and 13C NMR Study of Pyrazole-4-Carboxaldehydes: J. Heterocyclic Chem., Bd. 30, 1993, pp. 957-960, XP002284479, Formula 19, p. 957.

Database Beilstein, Beilstein Institute for Organic Chemistry, Frankfurt-Main, DE; Jan. 24, 2002, XP002284482, Database Accession No. BRN 8913586 & Bratenko et al: Russ. J. Org. Chem. EN, Bd. 37, Nr. 4, 2001, pp. 552-555.

Caramella, et al., Heterocycles, vol. 40, No. 2, 1995, pp. 515-520.

Non Final Rejection dated May 7, 2007—U.S. Appl. No. 10/552,064, filed Oct. 5, 2005 (Publication No. US-2007-0010531-A1).

Non Final Rejection dated Sep. 29, 2007—U.S. Appl. No. 10/552,064, filed Oct. 5, 2005 (Publication No. US-2007-0010531-A1).

Final Rejection dated Jul. 9, 2008—U.S. Appl. No. 10/552,064, filed Oct. 5, 2005 (Publication No. US-2007-0010531-A1).

Non Final Rejection dated Nov. 20, 2007—U.S. Appl. No. 10/551,998, filed Oct. 5, 2006 (Publication No. US-2007-0105871-A1).

Final Rejection dated Aug. 7, 2008—U.S. Appl. No. 10/551,998, filed Oct. 5, 2006 (Publication No. US-2007-0105871-A1).

Non Final Rejection dated Aug. 25, 2008—U.S. Appl. No. 10/552,065, filed Oct. 5, 2005 (Publication No. US-2006-0264419-A1).

O'Brian et al: "Some Reactions of 3-Hydroxy-1-Phenylpyrazole" J. Org. Chem., Bd.31, 1966, pp. 1538-1542, XP002284477, The Entire Document.

* cited by examiner

PYRAZOLE COMPOUNDS

The invention relates to compounds of the formula I

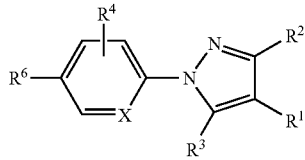

in which
$R^2$, $R^4$ denote H, A, Hal, cycloalkyl having 3 to 7 C atoms, $CF_3$, $NO_2$, CN, $OCF_3$, OA, NHA, $NA_2$, $NH_2$,
$R^3$, $R^6$ denote $(CH_2)_n$Het, $(CH_2)_n$Ar,
$R^1$ denotes H or an organic radical, in particular $(CH_2)_n CO_2R^5$, $(CH_2)_n$COHet, CHO, $(CH_2)_n OR^5$, $(CH_2)_n$Het, $(CH_2)_n N(R^5)_2$, CH=N-OA, $CH_2$CH=NOA, $(CH_2)_n$NHOA, $(CH_2)_n(R^5)$Het, $(CH_2)_n$CH=N-Het, $(CH_2)_n$O-COR$^5$, $(CH_2)_n N(R^5)CH_2CH_2OR^5$, $(CH_2)_n N(R^5)CH_2CH_2OCF_3$, $(CH_2)_n N(R^5)C(R^5)COOR^5$, $(CH_2)_n N(R^5)CH_2COHet$, $(CH_2)_n N(R^5)CH_2$Het, $(CH_2)_n N(R^5)CH_2CH_2$Het, $(CH_2)_n N(R^5)CH_2CH_2N(R^5)CH_2COOR^5$, $(CH_2)_n N(R^5)CH_2CH_2N(R^5)_2$, CH=CHCOOR$^5$, CH=CHCH$_2$NR$^5$Het, CH=CHCH$_2$N(R$^5$)$_2$, CH=CHCH$_2$OR$^5$ or $(CH_2)_n N(R^5)$Ar,
$R^5$ denotes H or A
A denotes straight-chain or branched alkyl or alkoxy having 1 to 10 C atoms, alkenyl or alkenyloxyalkyl having 2 to 10 C atoms,
Het denotes an organic radical, in particular a saturated, unsaturated or aromatic mono- or bicyclic heterocyclic or linear or branched organic radical containing one or more hetero atoms which is unsubstituted or mono- or polysubstituted by A and/or Hal,
Ar denotes an organic aromatic radical, in particular a phenyl radical which is unsubstituted or mono- or polysubstituted by A and/or Hal, OR$^5$, OOCR$^5$, COOR$^5$, CON(R$^5$)$_2$, CN, NO$_2$, NH$_2$, NHCOR$^5$, CF$_3$, SO$_2$CH$_3$ or a ring-forming group —OCH$_2$O—, —O(CH$_2$)$_2$O— or —OC(CH$_3$)$_2$O—,
n denotes 0, 1, 2, 3, 4 or 5
and
Hal denotes F, Cl, Br or I
where, in the case that X has the meaning CH, $R^2$ and $R^4$ do not simultaneously denote H,
and salts and solvates, enantiomers, racemates thereof and other mixtures of the enantiomers, in particular physiologically tolerated salts and solvates thereof.

The invention had the object of finding novel compounds having valuable properties, in particular those which can be used for the preparation of medicaments.

It has been found that the compounds of the formula I and salts and solvates thereof have very valuable pharmacological properties and are well tolerated.

The invention relates, in particular, to the compounds mentioned in the examples, which have the properties and potential uses of the compounds of the formula I that are outlined in the present application.

In particular, the compounds of the formula I according to the invention are suitable as ligands of 5 HT receptors, and consequently the compounds according to the invention, and salts and solvates, enantiomers and racemates thereof, in particular physiologically tolerated salts and solvates thereof, are suitable for the treatment and prophylaxis of diseases which can be influenced by the binding of the compounds of the formula I to 5 HT receptors.

Similar compounds are disclosed, for example, in DE 2201889, DE 2258033 or DE 2906252.

In particular, the compounds of the formula I according to the invention are suitable as ligands of 5 HT2A and/or 5HT2C receptors and can be used in human and veterinary medicine for the prophylaxis and treatment of various diseases of the central nervous system, such as, for example, schizophrenia, depression, dementia, dyskinesia, Parkinson's disease, Alzheimer's disease, Lewy bodies dementia, Huntington's, Tourette's syndrome, anxiety, learning and memory impairments, neurodegenerative diseases and other cognitive impairments, as well as nicotine dependence and pain.

The compounds of the formula I and/or physiologically acceptable salts or solvates thereof are particularly preferably used for the preparation of a medicament for the prophylaxis and/or treatment of psychoses, neurological disorders, amyotrophic lateral sclerosis, eating disorders, such as bulimia, anorexia nervosa, of premenstrual syndrome and/or for positively influencing obsessive-compulsive disorder (OCD).

It has been found that the compounds of the formula I and physiologically acceptable salts and solvates thereof, while being well tolerated, have valuable pharmacological properties since they have actions on the central nervous system. The compounds have strong affinity to 5-HT$_{2A}$ receptors, they furthermore exhibit 5-HT$_{2A}$ receptor-antagonistic properties.

Preference is therefore given to the use of the compounds of the formula I and/or physiologically acceptable salts and solvates thereof for the preparation of a medicament having a 5-HT receptor-antagonistic action, in particular a 5-HT$_{2A}$ receptor-antagonistic action.

For in-vitro detection of the affinity to 5-HT$_{2A}$ receptors, the following test (Example A1), for example, can be used. The 5-HT$_{2A}$ receptors are exposed both to [$^3$H]ketanserine (a substance known for its affinity to the receptor) and also to the test compound. The decrease in the affinity of [$^3$H]ketanserine to the receptor is an indication of the affinity of the test substance to the 5-HT$_{2A}$ receptor. The detection is carried out analogously to the description by J. E. Leysen et al., Molecular Pharmacology, 1982, 21: 301-314, or as also described, for example, in EP 0320983.

The efficacy of the compounds according to the invention as 5-HT$_{2A}$ receptor antagonists can be measured in vitro analogously to W. Feniuk et al., Mechanisms of 5-hydroxytryptamine-induced vasoconstriction, in: The Peripheral Actions of 5-Hydroxytryptamine, ed. Fozard J R, Oxford University Press, New York, 1989, p. 110. Thus, the contractility of the rat tail artery caused by 5-hydroxytryptamine is mediated by 5-HT$_{2A}$ receptors. For the test system, vessel rings prepared from the ventral rat tail artery are subjected to perfusion in an organ bath containing an oxygen-saturated solution. By introducing increasing concentrations of 5-hydroxytryptamine into the solution, a response is obtained to the cumulative concentration of 5-HT. The test compound is then added to the organ bath in suitable concentrations, and a second concentration curve for 5-HT is measured. The strength of the test compound in shifting the 5-HT-induced concentration curve to higher 5-HT concentrations is a measure of the 5-HT$_{2A}$ receptor-antagonistic property in vitro.

The 5-HT$_{2A}$-antagonistic property can be determined in vivo analogously to M. D. Serdar et al., Psychopharmacology, 1996, 128: 198-205.

The compounds of the formula I are therefore suitable both in veterinary and in human medicine for the treatment of functional disorders of the central nervous system and of inflammation. They can be used for the prophylaxis of and for combating the consequences of cerebral infarction phenomena (apoplexia cerebri), such as strokes and cerebral ischaemia, and for the treatment of extrapyramidal motor side effects of neuroleptics and of Parkinson's disease, for the acute and symptomatic therapy of Alzheimer's disease and for the treatment of amyotrophic lateral sclerosis. They are likewise suitable as therapeutic agents for the treatment of brain and spinal cord traumas. In particular, however, they are suitable as medicament active ingredients for anxiolytics, antidepressants, antipsychotics, neuroleptics, antihypertonics and/or for positively influencing obsessive-compulsive disorder (OCD; for example WO 9524194), anxiety states and physiological changes associated with anxiety states, such as, for example, tachycardia, tremor or sweating (for example EP 319962), panic attacks, psychoses, schizophrenia, anorexia, delusional obsessions, agoraphobia, migraine, Alzheimer's disease, sleep disorders, including sleep apnoea, tardive dyskinesia, learning disorders, age-dependent memory disorders, eating disorders, such as bulimia, drugs misuse, such as, for example, of alcohol, opiates, nicotine, psychostimulants, such as, for example, cocaine or amphetamines (for example U.S. Pat. No. 6,004,980), sexual dysfunctions, conditions of pain of all types and fibromyalgia (for example WO 9946245). The compounds of the formula I are suitable for the treatment of extrapyramidal side effects (EPS) in neuroleptic drug therapy. EPS is characterised by Parkinson's-like syndromes, acathisia and dystonic reactions (for example EP 337136). They are furthermore suitable for the treatment of anorexia nervosa, angina, Reynaud's, coronary vasospasms, in the prophylaxis of migraine (for example EP 208235), pain and neuralgia (for example EP 320983), for the treatment of Rett syndrome with autistic traits, of Asperger's syndrome, of autism and autistic disorders, in concentration deficit states, developmental disorders, hyperactivity states with mental underdevelopment and stereotypical behaviour states (for example WO 9524194).

They are furthermore suitable for the treatment of endocrine diseases, such as hyperprolactinaemia, furthermore in vasospasms, thrombotic diseases (for example WO 9946245), hypertension and gastrointestinal diseases.

They are furthermore suitable for the treatment of cardiovascular diseases and extrapyramidal symptoms, as described in WO 99/11641 on page 2, line 24-30.

The compounds according to the invention are furthermore suitable for reducing the intraocular pressure and for the treatment of glaucoma. They are also suitable for the prophylaxis and treatment of poisoning phenomena on administration of ergovaline to animals.

The compounds are furthermore suitable for the treatment of diseases of the cardiovascular system (WO 99/11641, page 3, line 14-15). The compounds according to the invention can also be employed together with other active ingredients in the treatment of schizophrenia. Suitable other active ingredients are the compounds mentioned in WO 99/11641 on page 13, line 20-26.

Other compounds which likewise exhibit 5-HT$_2$-antagonistic actions are described, for example, in EP 0320983.

WO 99/11641 describes phenylindole derivatives having 5-HT$_2$-antagonistic properties.

However, none of the above-mentioned documents describes the compounds of the formula I according to the invention or the use thereof as ligands of 5 HT receptors.

The compounds of the formula I can be employed as medicament active ingredients in human and veterinary medicine. They can furthermore be employed as intermediates for the preparation of further medicament active ingredients.

The invention accordingly relates to the compounds of the formula I and to the use thereof in human and animal medicine.

The present invention furthermore relates to a process for the preparation of compounds of the formula IA

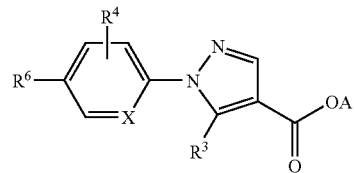

and salts and solvates thereof, which is characterised in that a compound of the formula II

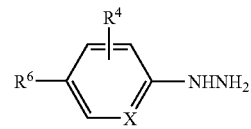

or acid-addition salts thereof
in which
$R^4$, $R^6$ and X have the meanings indicated above,
is reacted with a compound of the formula III

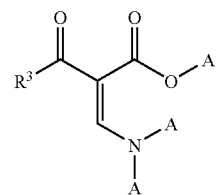

in which
A and $R^3$ have the meanings indicated above,
and/or in that a basic compound of the formula IA is converted into one of its salts by treatment with an acid.

The present invention furthermore relates to a process for the preparation of compounds of the formula IB

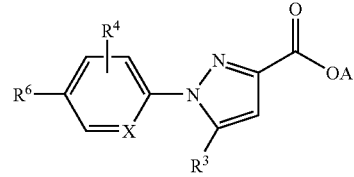

and salts and solvates thereof, which is characterised in that a compound of the formula II

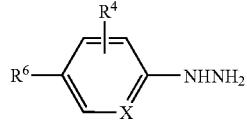

II or acid-addition salts thereof
in which
$R^4$, $R^6$ and X have the meanings indicated above,
is reacted with a compound of the formula IV

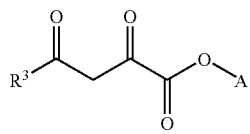

IV in which
A and $R^3$ have the meanings indicated above,
and/or in that a basic compound of the formula IB is converted into one of its salts by treatment with an acid.

The compounds of the formulae IA and IB can be converted into the further compounds of the formula I by conventional methods. In particular, the compounds of the formula IA and IB can be converted, using reducing agents, such as, for example, lithium aluminium hydride, into the corresponding alcohols of the formulae IC and ID

IC

ID

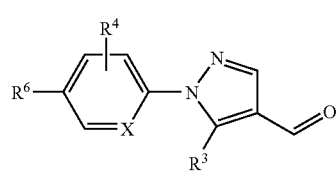

which can be oxidised, for example using $MnO_2$, to the compounds IE and IF.

IE

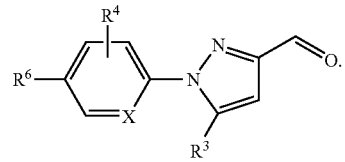

IF

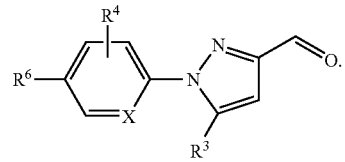

The compounds of the formulae IE and IF can themselves be aminated by known processes using corresponding nucleophiles, such as, for example, nitrogen bases, in particular hydroxylamine, O-methylhydroxylamine, morpholine, piperidine, piperazine, N-methylpiperazine, 4-methylpiperazin-1-ylamine, pyrrolidine, pyrazolidine or imidazolidine, optionally in the presence of a reducing agent, such as sodium triacetoxyborohydride, or converted into the corresponding imines. Furthermore, the compounds of the formulae IE and IF can be converted, by Wittig reaction with methoxymethyltriphenylphosphonium salts, into the corresponding enol ethers, which can be converted into the homologised aldehydes IG and H

IG

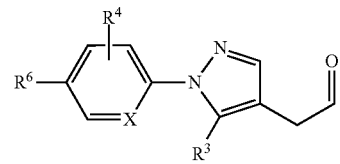

IH

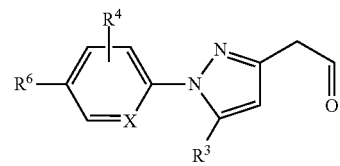

by treatment with an acid. The compounds of the formula IG and IH can be converted into the further compounds of the formula I analogously to the compounds of the formulae IE and IF.

The invention likewise relates to the novel compounds of the formula II, III, IV and V.

Solvates of the compounds of the formula I are taken to mean adductions of inert solvent molecules onto the compounds of the formula I which form owing to their mutual attractive force. Solvates are, for example, mono- or dihydrates or alcoholates.

Above and below, the radicals X, A, Ar, Het, n, $R^1$, $R^2$, $R^3$, $R^4$, $R^5$ and $R^6$ have the meanings indicated for the formula I, unless expressly stated otherwise.

X preferably denotes N.

$R^6$ preferably stands for $(CH_2)_n Ar$, in particular for Ar. $R^5$ very particularly preferably denotes phenyl, 2-, 3- or 4-cyanophenyl, 2-, 3- or 4-fluorophenyl, 2-, 3- or 4-methyl-, ethyl-, n-propyl- or n-butylphenyl, 2,3-, 2,4-, 2,5-, 2,6-, 3,4-, 3,5- or 3,6-difluoro-, dichloro- or dicyanophenyl, 3,4,5-trifluorophenyl, 3,4,5-trimethoxy- or triethoxyphenyl, thiophen-2-yl or thiophen-3-yl.

$R^3$ preferably denotes $(CH_2)_n Het$ or $(CH_2)_n Ar$, in particular $(CH_2)_n Ar$. $R^3$ very particularly preferably denotes phenyl, 2-, 3- or 4-cyanophenyl, 2-, 3- or 4-fluorophenyl, 2-, 3- or 4-methyl-, ethyl-, n-propyl- or n-butylphenyl, 2,3-, 2,4-, 2,5-, 2,6-difluoro- or dicyanophenyl, thiophen-2-yl or thiophen-3- yl, 2-, 3- or 4-pyridyl, 2-, 4- or 5-oxazolyl, 2-, 4- or 5-thiazolyl, quinolinyl, isoquinolinyl, 2- or 4-pyridazyl, 2-, 4- or 5-pyrimidyl, 2- or 3-pyrazinyl or 2- or 3-furanyl.

If $R^1$ denotes H, $R^2$ preferably has the meaning Hal, CN or alkyl having 1 to 7 C atoms, but in particular methyl, ethyl. If $R^2$ denotes H, $R^1$ preferably has the meaning $(CH_2)_nCO_2R^5$, $(CH_2)_nCO$-Het, CHO, $CH_2OR^5$, $(CH_2)_n$-Het, $(CH_2)_nN(R^5)_2$ or CH=N—OA, but in particular $(CH_2)_nCO_2R^5$, $(CH_2)_nCO$-Het, CHO, CH=N—OA or $(CH_2)_n$-Het. $R^2$ particularly preferably denotes H.

Further preferred meanings of $R^1$ and $R^2$ arise from the examples.

$R^4$ preferably denotes H, Hal, CN, A or $NO_2$, in particular H or Hal.

$R^5$ preferably has the meaning A.

$R^6$ preferably denotes $(CH_2)_nAr$, in particular Ar.

A preferably denotes alkyl, is preferably unbranched and has 1, 2, 3, 4, 5, 6, 7, 8, 9 or 10 C atoms, preferably 1, 2, 3, 4, 5 or 6 C atoms, and preferably denotes methyl, ethyl, n- or propyl, furthermore preferably isopropyl, butyl, isobutyl, sec-butyl or tert-butyl, but also n-pentyl, neopentyl, isopentyl or n-hexyl. Particular preference is given to methyl, ethyl, n-propyl, isopropyl, n-butyl, n-pentyl, n-hexyl or n-decyl.

A furthermore preferably has the meaning of the $(CH_2)_mOCH_3$ or $(CH_2)_mC_2H_5$ group, in which m denotes 2, 3, 4, 5 or 6, but in particular 2.

If A denotes alkenyl, it preferably stands for alkyl, 2- or 3-butenyl, isobutenyl, sec-butenyl, furthermore preferably 4-pentenyl, isopentenyl or 5-hexenyl.

Het is preferably an aromatic and in particular saturated heterocyclic radical which is unsubstituted or substituted by A. Het preferably denotes 1-piperidyl, 1-piperazyl, 1-(4-methyl)piperazyl, 1-(4-ethyl)piperazinyl, 1-(4-cyclopentyl)piperazinyl, 4-methylpiperazin-1-ylamine, 1-pyrrolidinyl, 1-pyrazolidinyl 1-(2-methyl)pyrazolidinyl, 1-imidazolidinyl or 1-(3-methyl)imidazolidinyl or 4-pyridyl, which may be unsubstituted or substituted by one or more CN group, 2- or 4-pyridazyl, 2-, 4- or 5-pyrimidyl, 2- or 3-pyrazinyl. Het furthermore preferably denotes a radical from the following table:

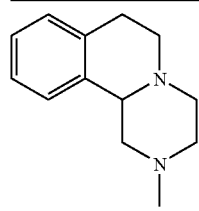
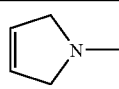
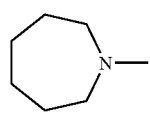
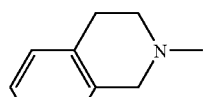
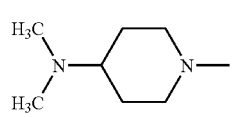
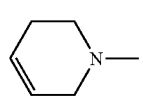
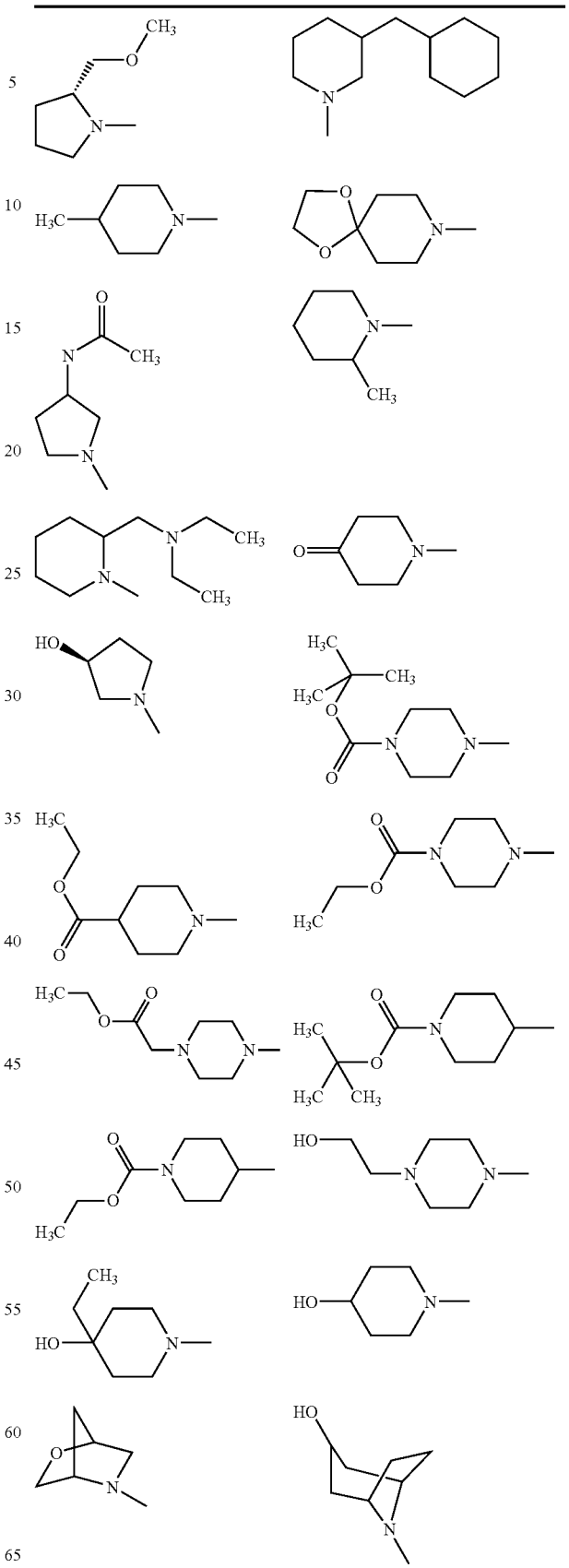

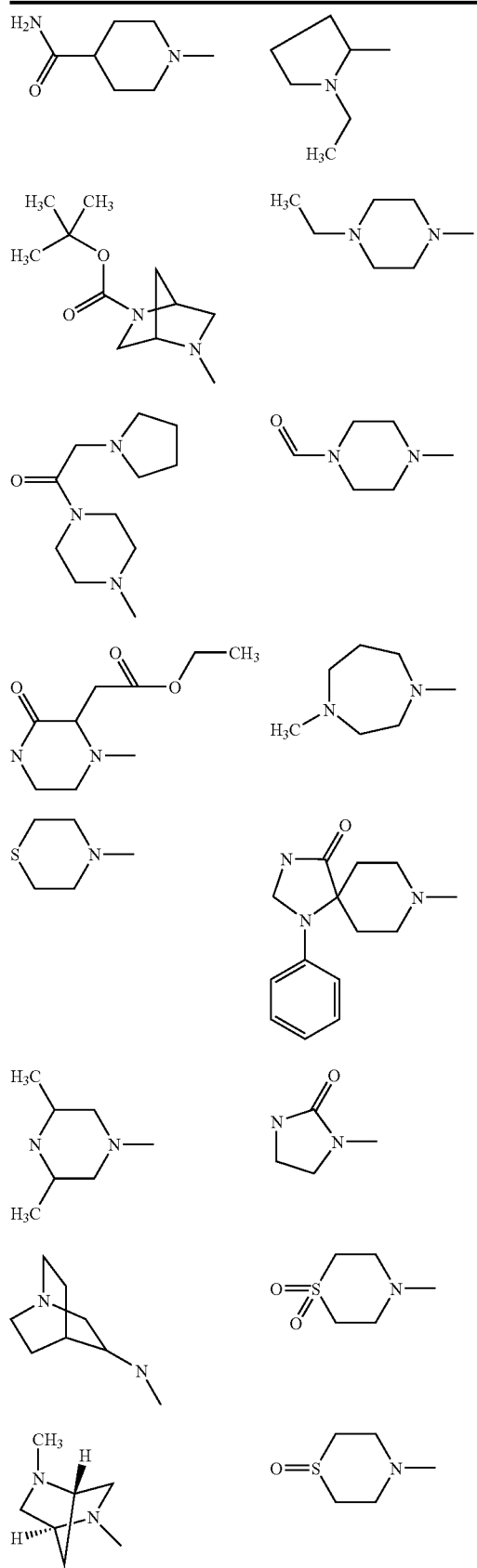
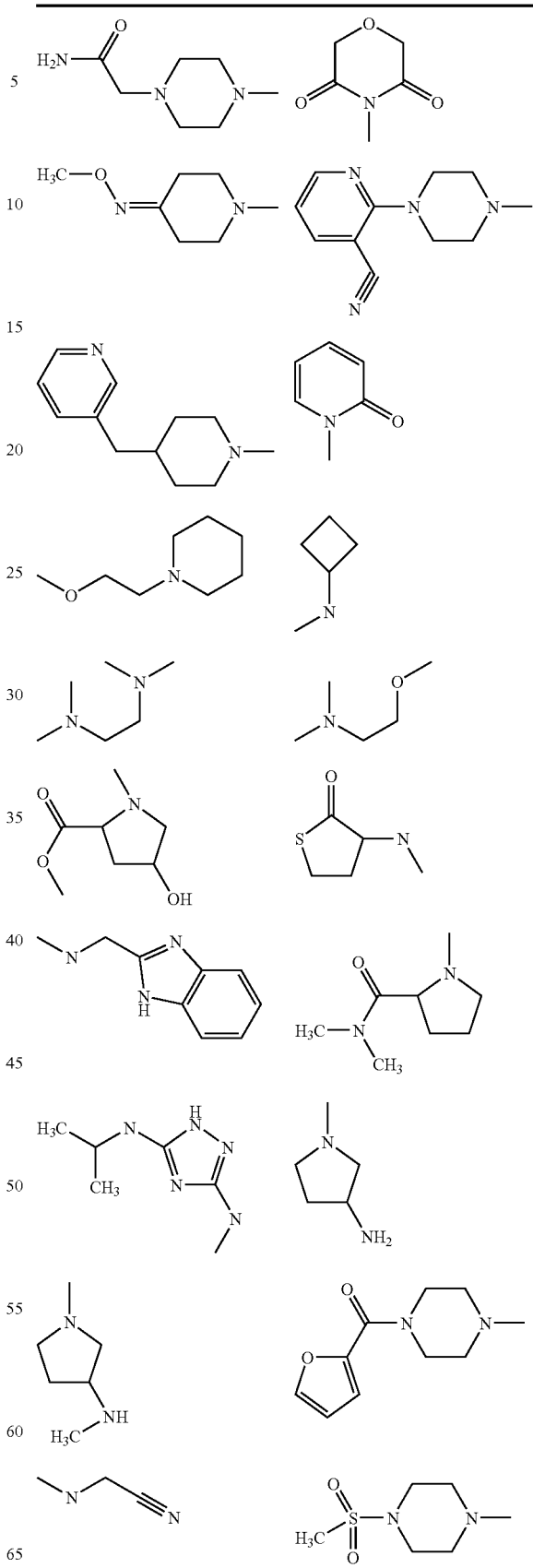

-continued

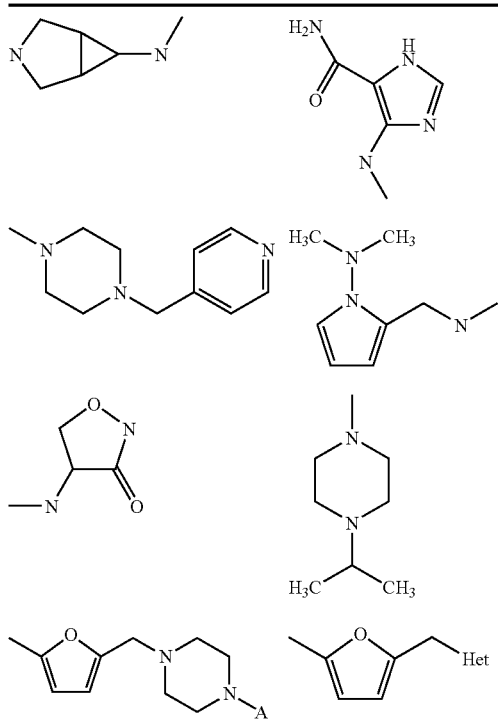

Het particularly preferably denotes one of the following radicals:

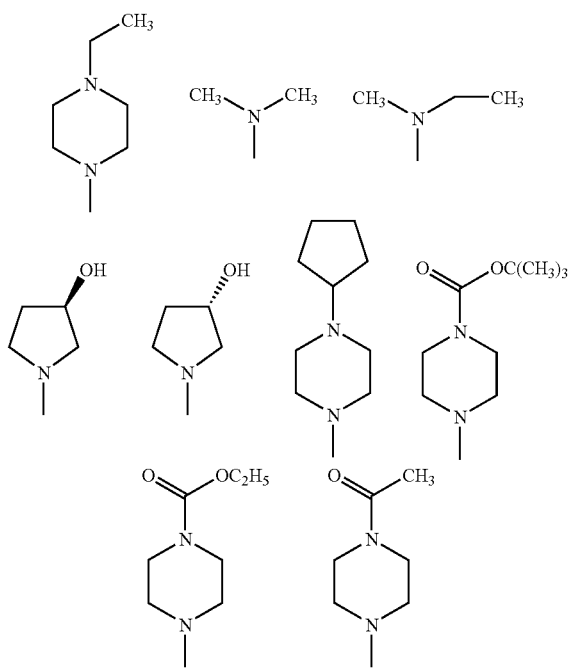

Ar preferably denotes a phenyl radical which is unsubstituted or substituted by Hal, OH, CN, $NO_2$, $NH_2$, $NHCOCH_3$, $COOCH_3$, $CONH_2$ or $CF_3$. Ar is preferably substituted in the 4- or 3-position.

n preferably denotes 0, 1 or 2, in particular 0 or 1.

Cycloalkyl preferably has 3-7 C atoms and preferably stands for cyclopropyl and cyclobutyl, furthermore preferably for cyclopentyl or cyclohexyl, furthermore also for cycloheptyl, particularly preferably cyclopentyl.

Hal preferably denotes F, Cl or Br, but also I.

If the compounds of the formula I has one or more chiral C atoms, the present invention relates to the enantiomers, diastereomers and mixtures thereof.

Throughout the invention, all radicals which occur more than once may be identical or different, i.e. are independent of one another.

Accordingly, the invention relates, in particular, to the compounds of the formula I in which at least one of the said radicals has one of the preferred meanings indicated above.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The compound of the formula III is preferably obtained by reaction of compounds of the formula V

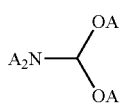

V in which A has the meaning indicated above,
with compounds of the formula VI

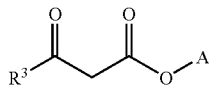

VI in which $R^3$ and A have the meaning indicated above,
under conditions known for such reactions.

The starting materials can, if desired, also be formed in situ by not isolating them from the reaction mixture, but instead immediately converting them further into the compounds of the formula I.

On the other hand, it is possible to carry out the reaction stepwise.

The starting materials of the formulae II, III and IV are generally known. If they are not known, they can be prepared by methods known per se.

Specifically, the reactions of the compounds of the formula II with the compounds of the formula III and the compounds of the formula IV are carried out in the presence or absence of a preferably inert solvent at temperatures between about −20 and about 150°, preferably between 20 and 100°.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF);

nitriles, such as acetonitrile; sulfoxides, such as dimethyl sulfoxide (DMSO); nitro compounds, such as nitromethane or nitrobenzene; esters, such as ethyl acetate, or mixtures of the said solvents.

The pH necessary for the reaction can be set in accordance with pH values selected for similar reactions of carbonyl compounds with amino compounds. The pH is preferably pre-specified through the use of the particular acid-addition salt, preferably a hydrogen halide addition salt, of the compound of the formula II, i.e. there is no additional addition of a base or acid to the reaction mixture. Preferred acid-addition salts are hydrochlorides or hydrobromides A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfuric acid. Salts with physiologically unacceptable acids, for example picrates, can be used for the isolation and/or purification of the compounds of the formula I.

On the other hand, if desired, the free bases of the formula I can be liberated from their salts using bases (for example sodium hydroxide, potassium hydroxide, sodium carbonate or potassium carbonate).

The invention relates, in particular, to compounds of the formula I and physiologically acceptable salts and solvates thereof as medicaments.

The invention also relates to the compounds of the formula I and physiologically acceptable salts and solvates thereof as glycine transporter inhibitors.

The invention furthermore relates to the use of the compounds of the formula I and/or physiologically acceptable salts and/or solvates thereof for the preparation of pharmaceutical compositions, in particular by non-chemical methods. In this case, they can be converted into a suitable dosage form together with at least one solid, liquid and/or semi-liquid excipient or adjuvant and, if desired, in combination with one or more further active ingredients.

The invention furthermore relates to pharmaceutical compositions comprising at least one compound of the formula I and/or one of its physiologically acceptable salts and/or solvates.

These compositions can be used as medicaments in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc, Vaseline. Suitable for oral administration are, in particular, tablets, pills, coated tablets, capsules, powders, granules, syrups, juices or drops, suitable for rectal administration are suppositories, suitable for parenteral administration are solutions, preferably oil-based or aqueous solutions, furthermore suspensions, emulsions or implants, suitable for topical application are ointments, creams or powders. The novel compounds may also be lyophilised and the resultant lyophilisates used, for example, for the preparation of injection preparations. The compositions indicated may be sterilised and/or comprise adjuvants, such as lubricants, preservatives, stabilisers and/or wetting agents, emulsifiers, salts for modifying the osmotic pressure, buffer substances, dyes, flavours and/or one or more further active ingredients, for example one or more vitamins.

In general, the substances according to the invention are preferably administered here in doses of between 1 and 500 mg, in particular between 5 and 100 mg, per dosage unit. The daily dose is preferably between about 0.02 and 10 mg/kg of body weight. However, the specific dose for each patient depends on a very wide variety of factors, for example on the efficacy of the specific compound employed, on the age, body weight, general state of health, sex, on the diet, on the time and method of administration, on the excretion rate, medicament combination and severity of the particular disease to which the therapy applies. Oral administration is preferred.

Preferred compounds of the formula I have nanomolar affinity to the 5 $HT_{2A}$ receptors. Particularly preferred compounds of the formula I have low affinity to the 5 HT2C receptor. Very particularly preferred compounds of the formula I exhibit no significant glycine transporter activity.

Above and below, all temperatures are indicated in ° C. In the following examples, "conventional work-up" means: water is added if necessary, the mixture is extracted with ethyl acetate or dichloromethane, the phases are separated, the organic phase is dried over sodium sulfate and evaporated, and the product is purified by chromatography on silica gel and/or by crystallisation.

EXAMPLE 1

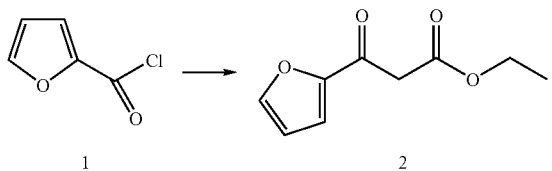

130 g of monoethyl malonate potassium salt are suspended in 2 l of ethyl acetate in a 6 l three-necked flask provided with stirrer, condenser, thermometer, dropping funnel and drying tube, 127 ml of triethylamine and 82.4 g of magnesium chloride (anhydrous) are added with cooling and stirring at 0° C., and the mixture is slowly warmed to 35-40° C. Stirring is continued at this temperature for 6 h, the mixture is again cooled to 0° C., and a solution of 50 ml of furan-2-carbonyl chloride in 1 l of ethyl acetate is added dropwise over the course of 15 minutes with cooling and stirring at 0° C. Stirring is continued overnight at RT, then 1.2 l of 13% hydrochloric acid are added dropwise with cooling and stirring, and the ethyl acetate phase is separated off. Conventional work-up gives the product 2 as slightly yellowish liquid. (b.p. 85° C./0.6-0.5 mbar).

EXAMPLE 2

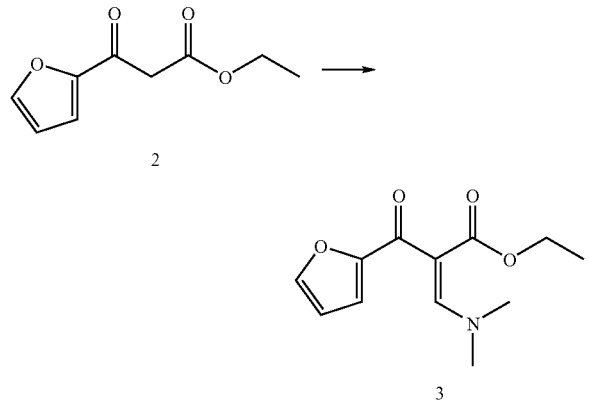

5 g of ethyl 2-furoylacetate are dissolved in 100 ml of THF, abs., in a 250 ml flask provided with magnetic stirrer, condenser and drying tube, 7.4 ml of N,N-dimethylformamide dimethyl acetal are added, and the mixture is stirred under reflux for 6 h. The reaction solution was then stripped off to give the residue 6.38 g (100%), giving 3.

EXAMPLE 3

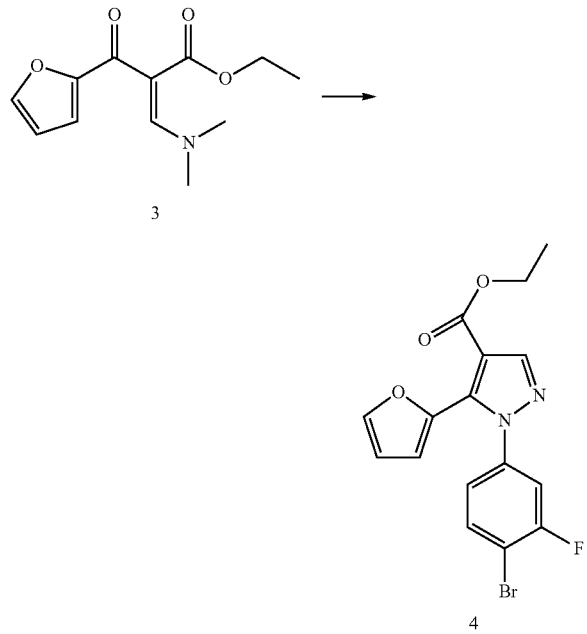

4.49 g of the beta-keto ester 3 are dissolved in 90 ml of abs. ethanol in a 250 ml one-necked flask provided with magnetic stirrer, condenser and drying tube, 4.2 g of 4-bromophenyl-hydrazinium chloride are added, and the mixture is stirred under reflux overnight. Conventional work-up gives 4.

EXAMPLE 4

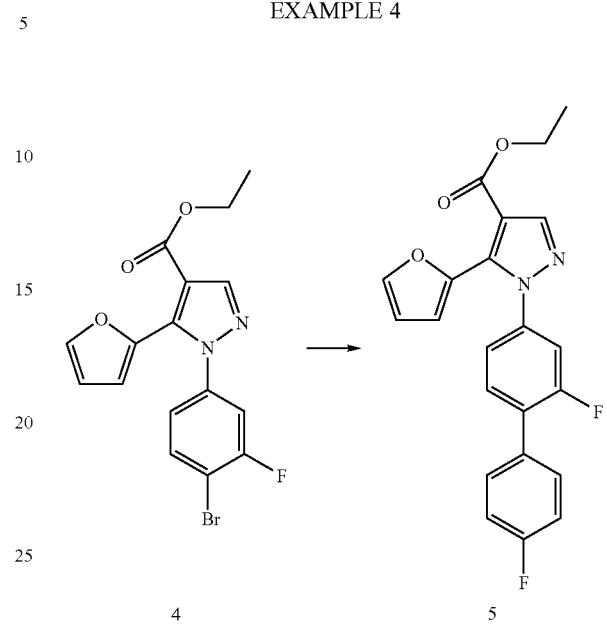

2.00 g of the aryl bromide 4 and 0.203 g of [1,1'-bis(diphenylphosphino)-ferocene)palladium(II) dichloride are dissolved successively in 80 ml of dimethoxyethane, 1.40 g of 4-fluorophenylboronic acid are added, and a solution of $Na_2CO_3$ in water (5.87 g in 25 ml) is subsequently added. The reaction solution is stirred overnight at RT. For work-up, the reaction batch is partitioned between diethyl ether and water. Conventional work-up gives 5.

EXAMPLE 5

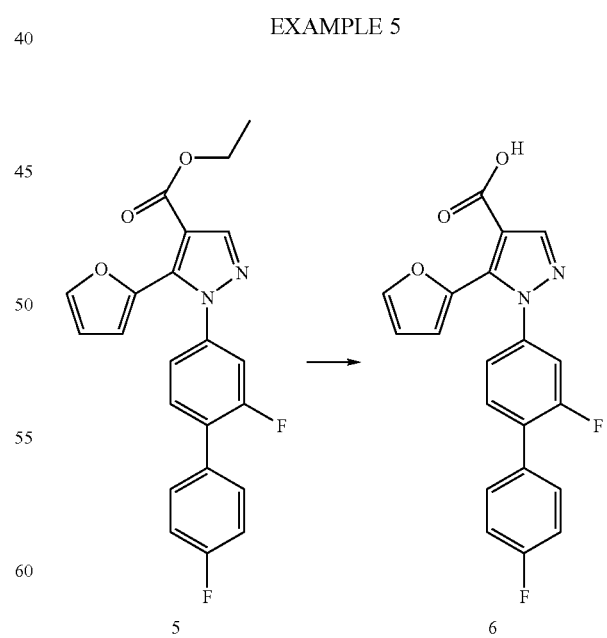

1.60 g of the ester 5 are initially introduced in THF, cooled to about 5 to 0° C., and 4.3 ml of a 1 M solution of $LiAlH_4$ in THF is subsequently slowly added dropwise. When the addition is complete, stirring is continued overnight at room temperature. Conventional work-up gives 6 crystalline solid.

EXAMPLE 6

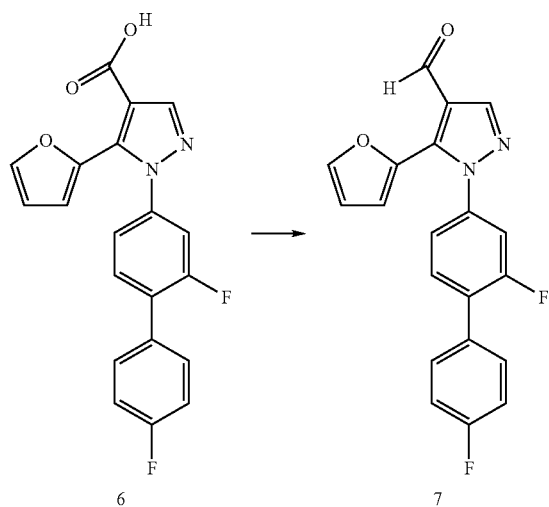

1.4 g of the alcohol 6 is dissolved in a mixture of 10 ml of THF and 40 ml of dichloromethane. 2.62 g of manganese dioxide are subsequently added, and the reaction batch is stirred overnight at RT. Conventional work-up gives the product 7 as crystalline solid.

EXAMPLE 7

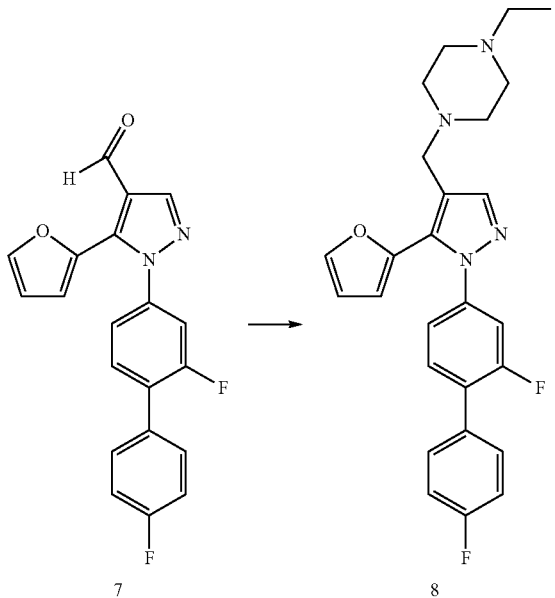

36 µl of $CH_3COOH$ are added to a mixture of 200 mg of the aldehyde 7, 103 mg of ethylpiperazine, 3.6 ml of 1,2-dichloroethane and 1.8 ml of THF. The mixture is stirred at room temperature for 3 h. 0.23 g of $NaB(OAc)_3H$ are subsequently added, and stirring is continued for 16 h.

Conventional work-up gives 1-ethyl-4-[1-(4'-fluorobiphenyl-4-yl)-5-furan-2-yl-1H-pyrazol-4-ylmethyl]piperazine dihydrochloride 8 as colourless solid.

The following compounds of the formula I are obtained analogously using the corresponding precursors:

EXAMPLES 8-51

(8) 1-[1-(3,4'-Difluorobiphenyl-4-yl)-5-furan-2-yl-1H-pyrazol-4-ylmethyl]-4-methylpiperazine
(9) 1-[1-(3,4'-Difluorobiphenyl-4-yl)-5-furan-2-yl-1H-pyrazol-4-ylmethyl]-4-ethylpiperazine
(10) 1-[1-(3,4'-Difluorobiphenyl-4-yl)-5-furan-2-yl-1H-pyrazol-4-ylmethyl]pyrrolidin-3-ol
(11) 1-[1-(3,4'-Difluorobiphenyl-4-yl)-5-furan-2-yl-1H-pyrazol-4-ylmethyl]piperazine
(12) [1-(3,4'-Difluorobiphenyl-4-yl)-5-furan-2-yl-1H-pyrazol-4-ylmethyl]dimethylamine
(13) [1-(3,4'-Difluorobiphenyl-4-yl)-5-furan-2-yl-1H-pyrazol-4-ylmethyl]ethylmethylamine
(14) [1-(3,4'-Difluorobiphenyl-4-yl)-5-furan-2-yl-1H-pyrazol-4-ylmethyl]methyl-(1-methylpyrrolidin-3-yl)amine
(15) 1-[1-(2,4'-Difluorobiphenyl-4-yl)-5-furan-2-yl-1H-pyrazol-4-ylmethyl]-4-methylpiperazine
(16) [1-(2,4'-Difluorobiphenyl-4-yl)-5-furan-2-yl-1H-pyrazol-4-ylmethyl]ethylmethylamine
(17) 1-[1-(4'-Fluorobiphenyl-4-yl)-3-methyl-5-phenyl-1H-pyrazol-4-ylmethyl]-4-methylpiperazine
(18) Ethyl-[1-(4'-fluorobiphenyl-4-yl)-3-methyl-5-phenyl-1H-pyrazol-4-ylmethyl]methylamine
(19) (1-Biphenyl-4-yl-3-methyl-5-phenyl-1H-pyrazol-4-yl)acetic acid ethyl ester
(20) 2-(1-Biphenyl-4-yl-3-methyl-5-phenyl-1H-pyrazol-4-yl)ethanol
(21) 1-{5-[2-(4'-Fluorobiphenyl-4-yl)-5-methyl-2H-pyrazol-3-yl]furan-2-ylmethyl}-4-methylpiperazine
(22) 1-Ethyl-4-{5-[2-(4'-fluorobiphenyl-4-yl)-5-methyl-2H-pyrazol-3-yl]-furan-2-ylmethyl}piperazine
(23) Ethyl-{5-[2-(4'-fluorobiphenyl-4-yl)-5-methyl-2H-pyrazol-3-yl]furan-2-ylmethyl}methylamine
(24) 1-{5-[2-(4'-Fluorobiphenyl-4-yl)-5-methyl-2H-pyrazol-3-yl]furan-2-ylmethyl}pyrrolidin-3-ol
(25) 1-[1-(4'-Fluorobiphenyl-4-yl)-3,5-dimethyl-1H-pyrazol-4-ylmethyl]-4-methylpiperazine
(26) 1-Ethyl-4-[1-(4'-fluorobiphenyl-4-yl)-3,5-dimethyl-1H-pyrazol-4-ylmethyl]piperazine
(27) Ethyl-[1-(4'-fluorobiphenyl-4-yl)-3,5-dimethyl-1H-pyrazol-4-ylmethyl]methylamine
(28) 1-[1-(4'-Fluorobiphenyl-4-yl)-5-methyl-1H-pyrazol-4-ylmethyl]-4-methylpiperazine
(29) 1-Ethyl-4-[1-(4'-fluorobiphenyl-4-yl)-5-methyl-1H-pyrazol-4-ylmethyl]piperazine
(30) 1-[1-(4'-Fluorobiphenyl-4-yl)-5-methyl-1H-pyrazol-4-ylmethyl]pyrrolidin-3-ol
(31) Ethyl-[1-(4'-fluorobiphenyl-4-yl)-5-methyl-1H-pyrazol-4-ylmethyl]-methylamine
(32) 1-[1-(4'-Fluorobiphenyl-4-yl)-3,5-dimethyl-1H-pyrazol-4-ylmethyl]-pyrrolidin-3-ol
(33) 1-[1-(4'-Fluorobiphenyl-4-yl)-1H-pyrazol-4-ylmethyl]pyrrolidin-3-ol
(34) 1-[1-(4'-Fluorobiphenyl-4-yl)-1H-pyrazol-4-ylmethyl]-4-methylpiperazine
(35) 1-Ethyl-4-[1-(4'-fluorobiphenyl-4-yl)-1H-pyrazol-4-ylmethyl]-piperazine
(36) 1-[1-(4'-Fluoro-2-methylbiphenyl-4-yl)-5-furan-2-yl-1H-pyrazol-4-ylmethyl]-4-methylpiperazine

(37) 1-Ethyl-4-[1-(4'-fluoro-2-methylbiphenyl-4-yl)-5-furan-2-yl-1H-pyrazol-4-ylmethyl]piperazine
(38) Ethyl-[1-(4'-fluoro-2-methylbiphenyl-4-yl)-5-furan-2-yl-1H-pyrazol-4-ylmethyl]methylamine
(39) 1-[1-(4'-Fluoro-2-methylbiphenyl-4-yl)-5-furan-2-yl-1H-pyrazol-4-ylmethyl]pyrrolidin-3-ol
(40) 1-[1-(2-Chloro-4'-fluorobiphenyl-4-yl)-5-furan-2-yl-1H-pyrazol-4-ylmethyl]-4-methylpiperazine
(41) 1-[1-(2-Chloro-4'-fluorobiphenyl-4-yl)-5-furan-2-yl-1H-pyrazol-4-ylmethyl]-4-ethylpiperazine
(42) 1-[1-(2-Chloro-4'-fluorobiphenyl-4-yl)-5-furan-2-yl-1H-pyrazol-4-ylmethyl]pyrrolidin-3-ol
(43) [1-(2-Chloro-4'-fluorobiphenyl-4-yl)-5-furan-2-yl-1H-pyrazol-4-ylmethyl]ethylmethylamine
(44) 1-[1-(4'-Fluoro-3-methylbiphenyl-4-yl)-5-furan-2-yl-1H-pyrazol-4-ylmethyl]-4-methylpiperazine
(45) 1-Ethyl-4-[1-(4'-fluoro-3-methylbiphenyl-4-yl)-5-furan-2-yl-1H-pyrazol-4-ylmethyl]piperazine
(46) 1-[1-(4'-Fluoro-3-methylbiphenyl-4-yl)-5-furan-2-yl-1H-pyrazol-4-ylmethyl]pyrrolidin-3-ol
(47) Ethyl-[1-(4'-fluoro-3-methylbiphenyl-4-yl)-5-furan-2-yl-1H-pyrazol-4-ylmethyl]methylamine
(48) 1-[5-Furan-2-yl-1-(2,6,4'-trifluorobiphenyl-4-yl)-1H-pyrazol-4-ylmethyl]-4-methylpiperazine
(49) 1-Ethyl-4-[5-furan-2-yl-1-(2,6,4'-trifluorobiphenyl-4-yl)-1H-pyrazol-4-ylmethyl]piperazine
(50) 1-[5-Furan-2-yl-1-(2,6,4'-trifluorobiphenyl-4-yl)-1H-pyrazol-4-ylmethyl]pyrrolidin-3-ol
(51) Ethyl-[5-furan-2-yl-1-(2,6,4'-trifluorobiphenyl-4-yl)-1H-pyrazol-4-ylmethyl]methylamine The examples below relate to pharmaceutical compositions:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l andsterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced in a conventional manner into hard gelatine capsules in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

EXAMPLE I

Inhalation Spray 14 g of active ingredient of the formula I are dissolved in 10 l of isotonic NaCl solution, and the solution is transferred into commercially available spray containers with pump mechanism. The solution can be sprayed into the mouth or nose. One spray shot (about 0.1 ml) corresponds to a dose of about 0.14 mg.

The invention claimed is:
1. A compound of formula I

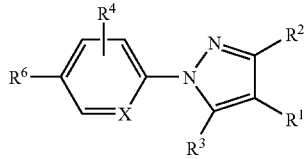

in which
R², R⁴ denote H, A, Hal, cycloalkyl having 3 to 7 C atoms, CF₃, NO₂, CN, OCF₃, OA, NHA, NA₂, or NH₂,
R⁶ is phenyl, 2-, 3- or 4-cyanophenyl, 2-, 3- or 4-fluorophenyl, 2-, 3- or 4-methyl-, ethyl-, n-propyl- or n-butylphenyl, 2,3-, 2,4-, 2,5-, 2,6-, 3,4-, 3,5- or 3,6-difluoro-, dichloro- or dicyanophenyl, 3,4,5-trifluorophenyl, 3,4,5-trimethoxy- or triethoxyphenyl, thiophen-2-yl or thiophen-3-yl,
R³ is phenyl, 2-, 3- or 4-cyanophenyl, 2-, 3- or 4-fluorophenyl, 2-, 3- or 4-methyl-, ethyl-, n-propyl- or n-butylphenyl, 2,3-, 2,4-, 2,5-, 2,6-difluoro- or dicyanophenyl, thiophen-2-yl or thiophen-3-yl, 2-, 3- or 4-pyridyl, 2-, 4- or 5-oxazolyl, 2-, 4- or 5-thiazolyl, quinolinyl, isoquinolinyl, 2- or 4-pyridazyl, 2-, 4- or 5-pyrimidyl, 2- or 3-pyrazinyl or 2- or 3-furanyl,
R¹ denotes CO₂R⁵, (CH₂)$_n$COHet, CHO, (CH₂)$_n$OR⁵, (CH₂)$_n$Het, (CH₂)$_n$N(R⁵)₂, CH=N-OA, CH₂CH=N-OA, (CH₂)$_n$NHOA, (CH₂)$_n$(R⁵)Het, (CH₂)$_n$CH=N-Het, (CH₂)$_n$OCOR', (CH₂)$_n$N(R⁵)CH₂CH₂OR⁵, (CH₂)$_n$N(R⁵)CH₂CH₂OCF₃, (CH₂)$_n$N(R⁵)C(R⁵)OCOR⁵, (CH₂)$_n$N(R')CH₂COHet, (CH₂)$_n$N(R⁵)CH₂Het, (CH₂)$_n$N(R⁵)CH₂CH₂Het, (CH₂)$_n$N(R⁵)CH₂CH₂N(R') CH₂OCOR', (CH₂)$_n$N(R⁵)CH₂CH₂N(R⁵)₂, CH=CHCOOR⁵, CH=CHCH₂NR⁵Het, CH=CHCH₂N(R⁵)₂, CH=CHCH₂OR⁵ or (CH₂)$_n$N(R⁵)Ar,
R⁵ denotes H or A
A denotes straight-chain or branched alkyl or alkoxy having 1 to 10 C atoms, or alkenyl or alkenyloxyalkyl having 2 to 10 C atoms,
Het is 1-piperidyl, 1-piperazyl, 1-(4-methyl)piperazyl, 1-(4-ethyl)piperazinyl, 1-(4-cyclopentyl)piperazinyl, 4-methylpiperazin-1-ylamine, 1-pyrrolidinyl, 1-pyrazolidinyl 1-(2-methyl)pyrazolidinyl, 1-imidazolidinyl or 1-(3-methyl)imidazolidinyl or 4-pyridyl, which is unsubstituted or substituted by one or more CN group, 2- or 4-pyridazyl, 2-, 4- or 5-pyrimidyl, 2- or 3-pyrazinyl, or a group of one of the formulae below

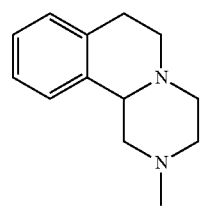
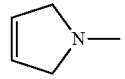
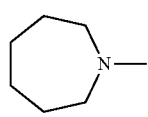
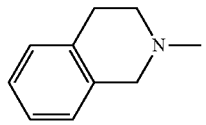
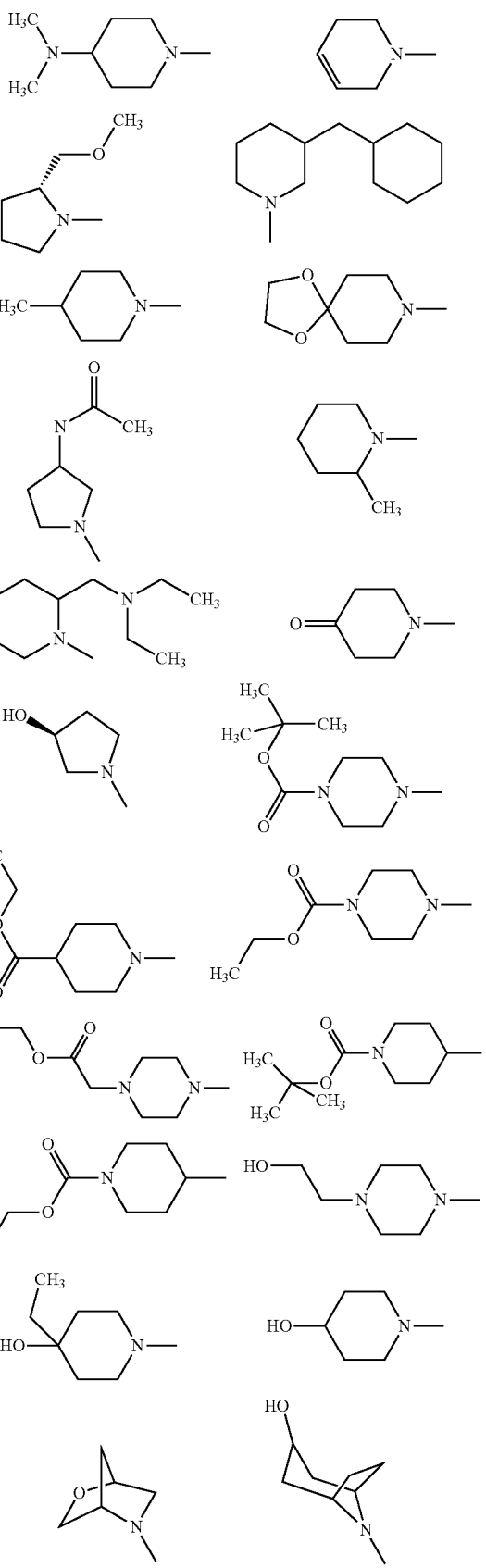

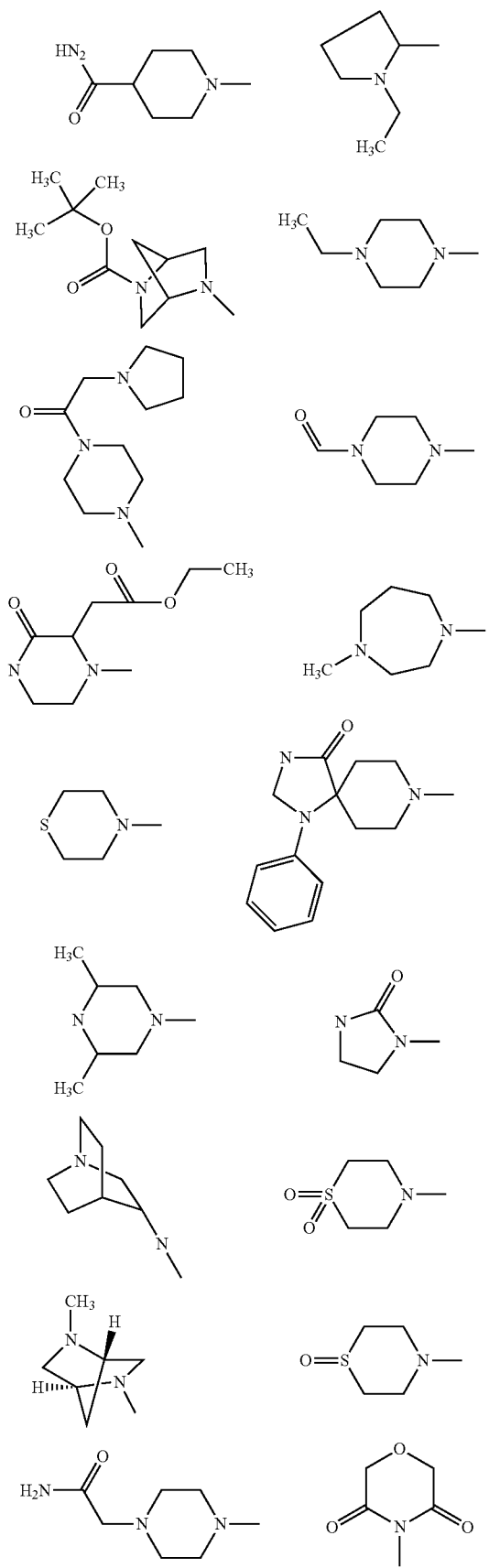
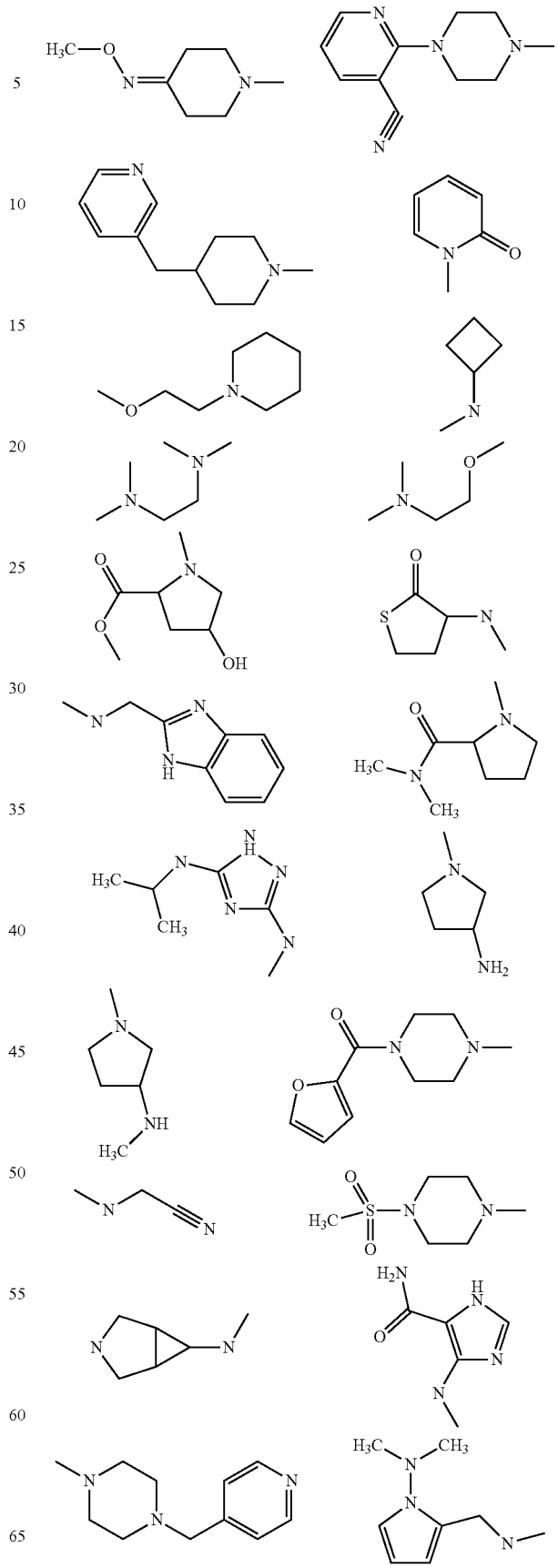

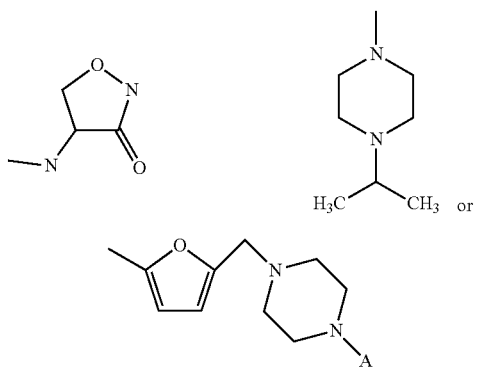

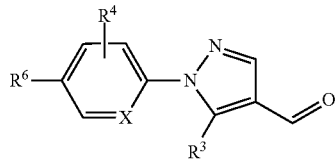

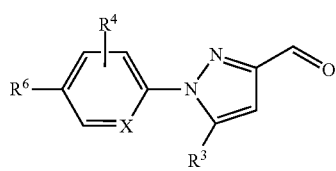

Ar denotes a phenyl radical which is unsubstituted or mono or polysubstituted by A and/or Hal, $OR^5$, $OOCR^5$, $COOR^5$, $CON(R^5)_2$, CN, $NO_2$, $NH_2$, $NHCOR^5$, $CF_3$ or $SO_2CH_3$, X denotes CH or N, n denotes 0, 1, 2, 3, 4 or 5 and Hal denotes F, Cl, Br or I, where, in the case that X has the meaning CH, $R^2$ and $R^4$ do not simultaneously denote H, or a salt, enantiomer, or racemate thereof, or a mixture of enantiomers.

2. A compound according to claim 1, in which X has the meaning N.

3. A compound of formula IA, IB, IC, ID, IE or IF:

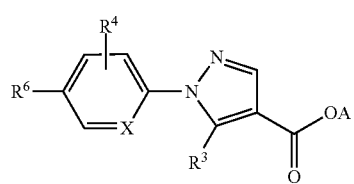
IA

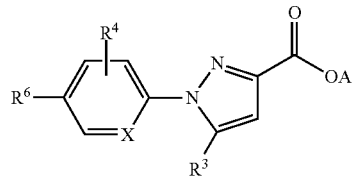
IB

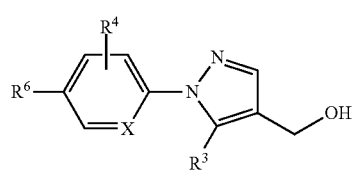
IC

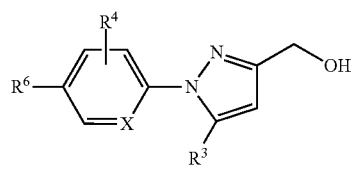
ID in which $R^3$ is phenyl, 2-, 3- or 4-cyanophenyl, 2-, 3- or 4-fluorophenyl, 2-, 3- or 4-methyl-, ethyl-, n-propyl- or n-butylphenyl, 2,3-, 2,4-, 2,5-, 2,6-difluoro- or dicyanophenyl, thiophen-2-yl or thiophen-3-yl, 2-, 3- or 4-pyridyl, 2-, 4- or 5-oxazolyl, 2-, 4- or 5-thiazolyl, quinolinyl, isoquinolinyl, 2- or 4-pyridazyl, 2-, 4- or 5-pyrimidyl, 2- or 3-pyrazinyl or 2- or 3-furanyl, $R^4$ denote H, A, Hal, cycloalkyl having 3 to 7 C atoms, $CF_3$, $NO_2$, CN, $OCF_3$, OA, NHA, $NA_2$ or $NH_2$, A denotes straight-chain or branched alkyl or alkoxy having 1 to 10 C atoms, or alkenyl or alkenyloxyalkyl having 2 to 10 C atoms, Hal denotes F, Cl, Br or I, X denotes CH or N, where, in the case that X has the meaning CH, $R^4$ in the compounds of formulae IA, IC and IE does not denote H, and $R^6$ is phenyl, 2-, 3- or 4-cyanophenyl, 2-, 3- or 4-fluorophenyl, 2-, 3- or 4-methyl-, ethyl-, n-propyl- or n-butylphenyl, 2,3-, 2,4-, 2,5-, 2,6-, 3,4-, 3,5- or 3,6-difluoro-, dichloro- or dicyanophenyl, 3,4,5-trifluorophenyl, 3,4,5-trimethoxy- or triethoxyphenyl, thiophen-2-yl or thiophen-3-yl.

4. A process for preparing a compound of claim 1, which is of formula IA

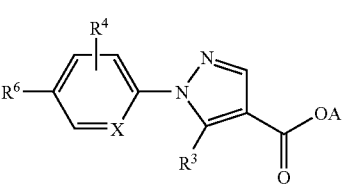
IA in which $R^3$, $R^4$, $R^6$, X and A have the meaning indicated for the compound of formula I or a salt thereof, comprising reacting a compound of formula II

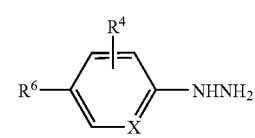
II or an acid-addition salt thereof,
in which $R^4$, $R^6$ and X have the meanings indicated for the compound of formula I, with a compound of formula III

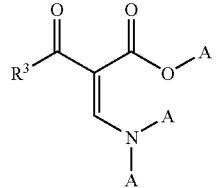

III in which A and $R^3$ have the meanings indicated for the compound of formula I,
and/or converting a basic compound of formula IA into one of its salts by treatment with an acid.

5. A process for preparing a compound of formula IB

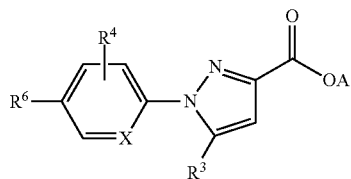

IB in which
$R^3$ is phenyl, 2-, 3- or 4-cyanophenyl, 2-, 3- or 4-fluorophenyl, 2-, 3- or 4-methyl-, ethyl-, n-propyl- or n-butylphenyl, 2,3-, 2,4-, 2,5-, 2,6-difluoro- or dicyanophenyl, thiophen-2-yl or thiophen-3-yl, 2-, 3- or 4-pyridyl, 2-, 4- or 5-oxazolyl, 2-, 4- or 5-thiazolyl, quinolinyl, isoquinolinyl, 2- or 4-pyridazyl, 2-, 4- or 5-pyrimidyl, 2- or 3-pyrazinyl or 2- or 3-furanyl,
$R^4$ denote H, A, Hal, cycloalkyl having 3 to 7 C atoms, $CF_3$, $NO_2$, CN, $OCF_3$, OA, NHA, $NA_2$ or $NH_2$,
A denotes straight-chain or branched alkyl or alkoxy having 1 to 10 C atoms, or alkenyl or alkenyloxyalkyl having 2 to 10 C atoms,
Hal denotes F, Cl, Br or I,
X denotes CH or N,
$R^6$ is phenyl, 2-, 3- or 4-cyanophenyl, 2-, 3- or 4-fluorophenyl, 2-, 3- or 4-methyl-, ethyl-, n-propyl- or n-butylphenyl, 2,3-, 2,4-, 2,5-, 2,6-, 3,4-, 3,5- or 3,6-difluoro-, dichloro- or dicyanophenyl, 3,4,5-trifluorophenyl, 3,4, 5-trimethoxy- or triethoxyphenyl, thiophen-2-yl or thiophen-3-yl,
or a salt thereof,
comprising reacting a compound of formula II

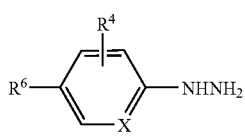

II or an acid-addition salt thereof,
in which $R^4$, $R^6$ and X have the meanings indicated for the compound of formula IB, with a compound of formula IV

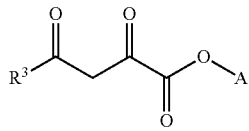

IV in which A and $R^3$ have the meanings indicated for the compound of formula IB, and/or converting a basic compound of formula IB into one of its salts by treatment with an acid.

6. A pharmaceutical composition comprising at least one compound of the formula I and/or one of its physiologically acceptable salts, and a pharmaceutically acceptable carrier,

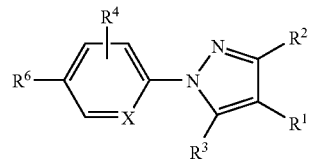

I in which
$R^2$, $R^4$ denote H, A, Hal, cycloalkyl having 3 to 7 C atoms, $CF_3$, $NO_2$, CN, $OCF_3$, OA, NHA, $NA_2$ or $NH_2$,
$R^6$ is phenyl, 2-, 3- or 4-cyanophenyl, 2-, 3- or 4-fluorophenyl, 2-, 3- or 4-methyl-, ethyl-, n-propyl- or n-butylphenyl, 2,3-, 2,4-, 2,5-, 2,6-, 3,4-, 3,5- or 3,6-difluoro-, dichloro- or dicyanophenyl, 3,4,5-trifluorophenyl, 3,4, 5-trimethoxy- or triethoxyphenyl, thiophen-2-yl or thiophen-3-yl,
$R^3$ is phenyl, 2-, 3- or 4-cyanophenyl, 2-, 3- or 4-fluorophenyl, 2-, 3- or 4-methyl-, ethyl-, n-propyl- or n-butylphenyl, 2,3-, 2,4-, 2,5-, 2,6-difluoro- or dicyanophenyl, thiophen-2-yl or thiophen-3-yl, 2-, 3- or 4-pyridyl, 2-, 4- or 5-oxazolyl, 2-, 4- or 5-thiazolyl, quinolinyl, isoquinolinyl, 2- or 4-pyridazyl, 2-, 4- or 5-pyrimidyl, 2- or 3-pyrazinyl or 2- or 3-furanyl,
$R^1$ denotes H or $CO_2R^5$, $(CH_2)_n$COHet, CHO, $(CH_2)_n OR^5$, $(CH_2)_n$Het, $(CH_2)_2 N(R^5)_2$, CH=N-OA, $CH_2$CH=N-OA, $(CH_2)_n$NHOA, $(CH_2)_n(R^5)$Het, $(CH_2)_n$CH=N-Het, $(CH_2)_n$OCOR', $(CH_2)_n N(R^5)CH_2CH_2OR^5$, $(CH_2)_n N(R^5)CH_2CH_2OCF_3$, $(CH_2)_n N(R^5)C(R^5)OCOR^5$, $(CH_2)_n N(R')CH_2$COHet, $(CH_2)_n N(R^5)CH_2$Het, $(CH_2)_n N(R^5)CH_2CH_2$Het, $(CH_2)_n N(R^5)CH_2CH_2N(R')CH_2OCOR'$, $(CH_2)_n N(R^5)CH_2CH_2N(R^5)_2$, CH=CHCOOR$^5$, CH=CHCH$_2$NR$^5$Het, CH=CHCH$_2$N(R$^5$)$_2$, CH=CHCH$_2$OR$^5$ or $(CH_2)_n$N(R$^5$)Ar,
$R^5$ denotes H or A
A denotes straight-chain or branched alkyl or alkoxy having 1 to 10 C atoms, or alkenyl or alkenyloxyalkyl having 2 to 10 C atoms,
Het is 1-piperidyl, 1-piperazyl, 1-(4-methyl)piperazyl, 1-(4-ethyl)piperazinyl, 1-(4-cyclopentyl)piperazinyl, 4-methylpiperazin-1-ylamine, 1-pyrrolidinyl, 1-pyrazolidinyl 1-(2-methyl)pyrazolidinyl, 1-imidazolidinyl or 1-(3-methyl)imidazolidinyl or 4-pyridyl, which is unsubstituted or substituted by one or more CN group, 2- or 4-pyridazyl, 2-, 4- or 5-pyrimidyl, 2- or 3-pyrazinyl, or a group of one of the formulae below

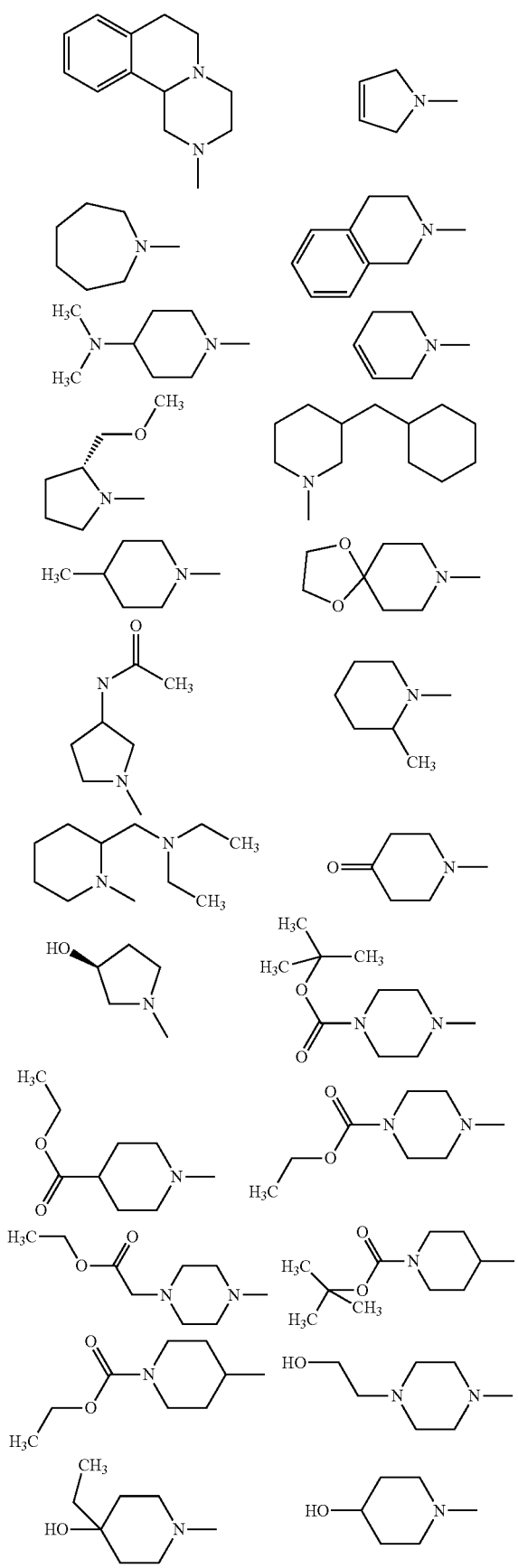
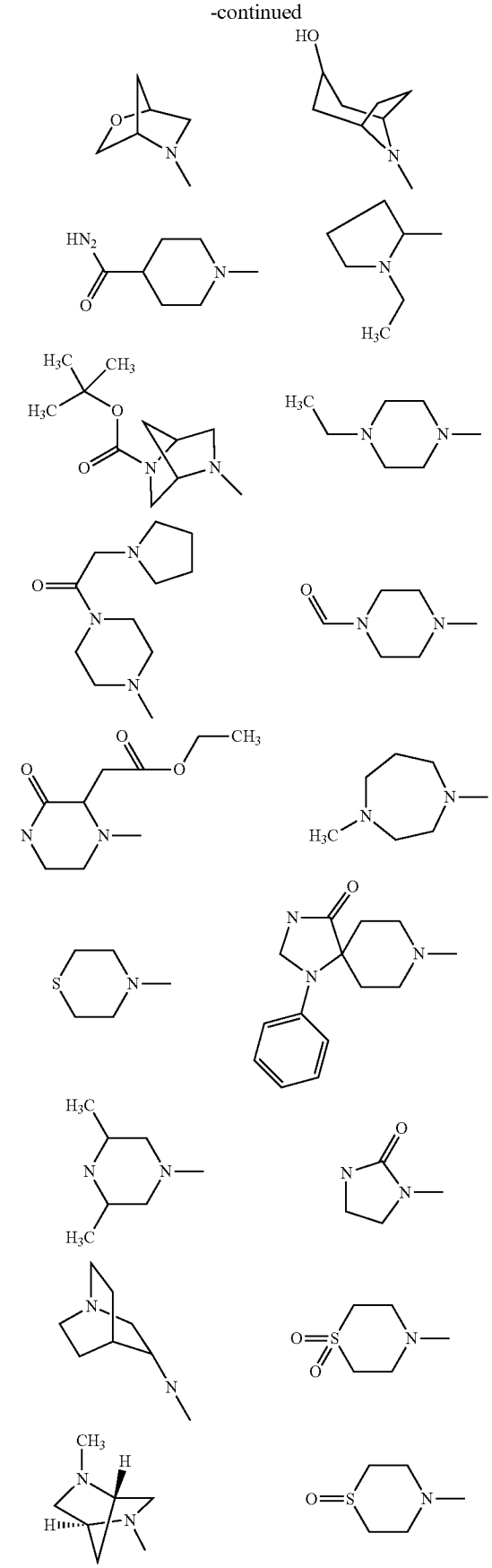

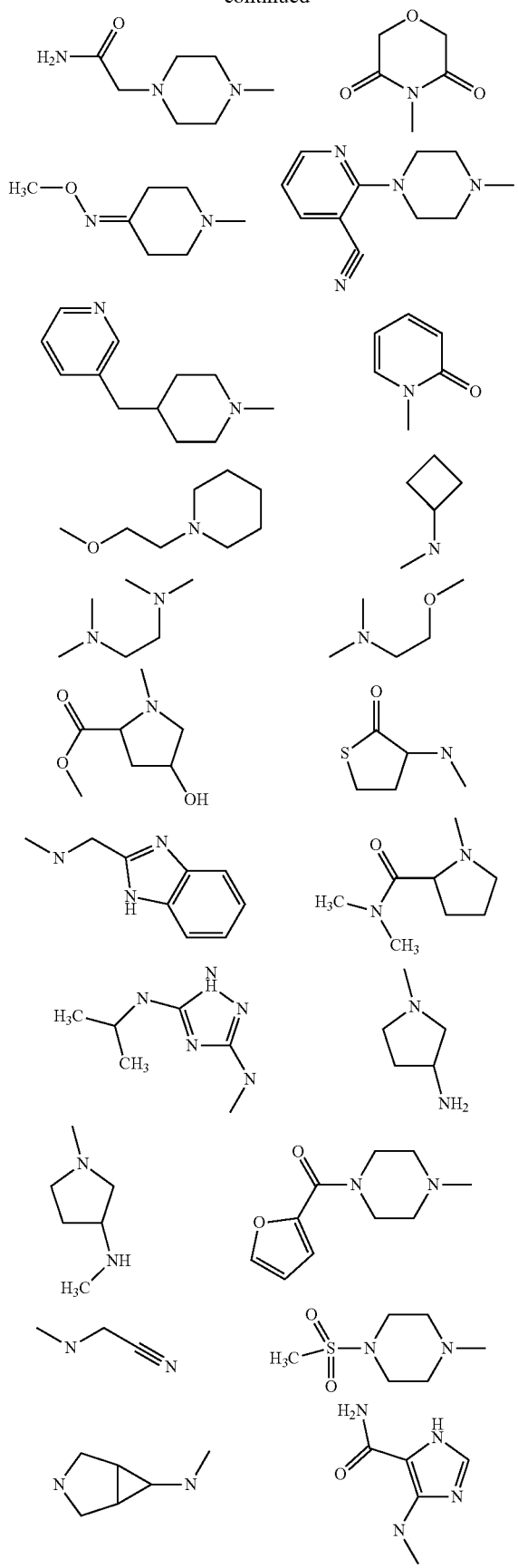
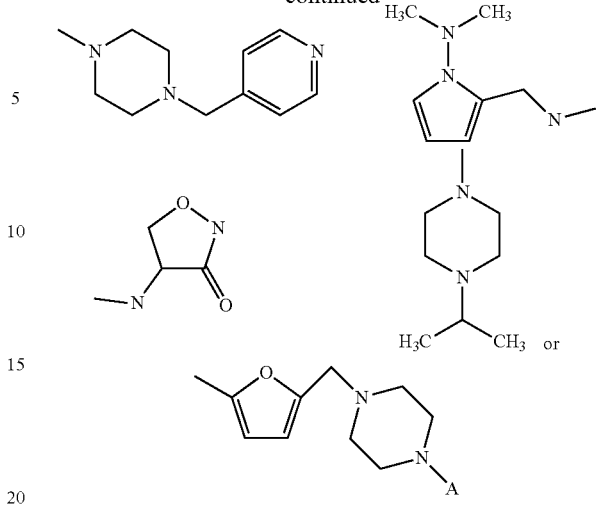

Ar denotes a phenyl radical which is unsubstituted or mono or polysubstituted by A and/or Hal, $OR^5$, $OOCR^5$, $COOR^5$, $CON(R^5)_2$, CN, $NO_2$, $NH_2$, $NHCOR^5$, $CF_3$ or $SO_2CH_3$, X denotes CH or N, n denotes 0, 1, 2, 3, 4 or 5 and Hal denotes F, Cl, Br or I, where, in the case that X has the meaning CH, $R^2$ and $R^4$ do not simultaneously denote H, or a salt, enantiomer, or racemate thereof, or a mixture of enantiomers.

7. A process for the preparation of a pharmaceutical composition, comprising combining a compound of the formula I according to claim 6 and/or one of its physiological acceptable salts into a suitable dosage form together with at least one solid, liquid or semi-liquid excipient or adjuvant.

8. A method for the in vitro inhibition of 5-HT2A receptor, comprising administering to said receptor a pharmaceutical composition according to claim 6.

9. A compound according to claim 1, in which $R^1$ denotes $(CH_2)_n COHet$, CHO, $(CH_2)_n OR^5$, $(CH_2)_n Het$, $(CH_2)_n N(R^5)_2$, CH=N-OA, $CH_2CH$=N-OA, $(CH_2)_n NHOA$, $(CH_2)_n (R^5)Het$, $(CH_2)_n CH$=N-Het, $(CH_2)_n OCOR'$, $(CH_2)_n N(R^5)CH_2CH_2OR^5$, $(CH_2)_n N(R^5)CH_2CH_2OCF_3$, $(CH_2)_n N(R^5)C(R^5)OCOR^5$, $(CH_2)_n N(R')CH_2COHet$, $(CH_2)_n N(R^5)CH_2Het$, $(CH_2)_n N(R^5)CH_2CH_2Het$, $(CH_2)_n N(R^5)CH_2CH_2N(R')CH_2OCOR'$, $(CH_2)_n N(R^5)CH_2CH_2N(R^5)_2$, CH=CHCOOR$^5$, CH=CHCH$_2$NR$^5$Het, CH=CHCH$_2$N(R$^5$)$_2$, CH=CHCH$_2$OR$^5$ or $(CH_2)_n N(R^5)Ar$.

10. A compound according to claim 1, in which $R^1$ denotes $CO_2R^5$, COHet, CHO, $(CH_2)_n OR^5$, $(CH_2)_n Het$, $(CH_2)_n N(R^5)_2$, CH=N-OA, $CH_2CH$=N-OA, $(CH_2)_n NHOA$, $(CH_2)_n (R^5)Het$, $(CH_2)_n CH$=N-Het, $(CH_2)_n OCOR'$, $(CH_2)_n N(R^5)CH_2CH_2OR^5$, $(CH_2)_n N(R^5)CH_2CH_2OCF_3$, $(CH_2)_n N(R^5)C(R^5)OCOR^5$, $(CH_2)_n N(R')CH_2COHet$, $(CH_2)_n N(R^5)CH_2Het$, $(CH_2)_n N(R^5)CH_2CH_2Het$, $(CH_2)_n N(R^5)CH_2CH_2N(R')CH_2OCOR'$, $(CH_2)_n N(R^5)CH_2CH_2N(R^5)_2$, CH=CHCOOR$^5$, CH=CHCH$_2$NR$^5$Het, CH=CHCH$_2$N(R$^5$)$_2$, CH=CHCH$_2$OR$^5$ or $(CH_2)_n N(R^5)Ar$.

11. A compound according to claim 1, in which $R^1$ denotes $(CH_2)_n Het$, $(CH_2)_n N(R^5)_2$, CH=N-OA, $CH_2CH$=N-OA, $(CH_2)_n NHOA$, $(CH_2)_n (R^5)Het$, $(CH_2)_n CH$=N-Het, $(CH_2)_n OCOR'$, $(CH_2)_n N(R^5)CH_2CH_2OR^5$, $(CH_2)_n N(R^5)$ $CH_2CH_2OCF_3$, $(CH_2)_n N(R^5)C(R^5)OCOR^5$, $(CH_2)_n N(R')CH_2COHet$, $(CH_2)_n N(R^5)CH_2Het$, $(CH_2)_n N(R^5)CH_2CH_2Het$, $(CH_2)_n N(R^5)CH_2CH_2N(R')CH_2OCOR'$, (CH$_2$)$_n$N(R$^5$)CH$_2$CH$_2$N(R$^5$)$_2$, CH=CHCOOR$^5$, CH=CHCH$_2$NR$^5$Het, CH=CHCH$_2$N(R$^5$)$_2$, CH=CHCH$_2$OR$^5$ or (CH$_2$)$_n$N(R$^5$)Ar.

12. A compound according to claim 1 or a pharmaceutically acceptable salt thereof.

13. A compound according to claim 1, in which R$^3$ is thiophen-2-yl or thiophen-3-yl, 2-, 4- or 5-oxazolyl, 2-, 4- or 5-thiazolyl, quinolinyl, isoquinolinyl, 2- or 4-pyridazyl, 2-, 4- or 5-pyrimidyl, 2- or 3-pyrazinyl or 2- or 3-furanyl.

14. A compound according to claim 1, in which R$^3$ is 2- or 3-furanyl.

15. A compound according to claim 1, in which R$^4$ denote A, Hal, cycloalkyl having 3 to 7 C atoms, CF$_3$, NO$_2$, CN, OCF$_3$, OA, NHA, NA$_2$, or NH$_2$.

16. A compound according to claim 1, in which A denotes straight-chain or branched alkyl or alkoxy having 3 to 10 C atoms, or alkenyl or alkenyloxyalkyl having 3 to 10 C atoms.

17. A compound of formula I

I in which
R$^2$, R$^4$ denote H, A, Hal, cycloalkyl having 3 to 7 C atoms, CF$_3$, NO$_2$, CN, OCF$_3$, OA, NHA, NA$_2$, or NH$_2$, R$^6$ is phenyl, 2-, 3- or 4-cyanophenyl, 2-, 3- or 4-fluorophenyl, 2-, 3- or 4-methyl-, ethyl-, n-propyl- or n-butylphenyl, 2,3-, 2,4-, 2,5-, 2,6-, 3,4-, 3,5- or 3,6-difluoro-, dichloro- or dicyanophenyl, 3,4,5-trifluorophenyl, 3,4,5-trimethoxy- or triethoxyphenyl, thiophen-2-yl or thiophen-3-yl, R$^3$ is phenyl, 2-, 3- or 4-cyanophenyl, 2-, 3- or 4-fluorophenyl, 2-, 3- or 4-methyl-, ethyl-, n-propyl- or n-butylphenyl, 2,3-, 2,4-, 2,5-, 2,6-difluoro- or dicyanophenyl, thiophen-2-yl or thiophen-3-yl, 2-, 3- or 4-pyridyl, 2-, 4- or 5-oxazolyl, 2-, 4- or 5-thiazolyl, quinolinyl, isoquinolinyl, 2- or 4-pyridazyl, 2-, 4- or 5-pyrimidyl, 2- or 3-pyrazinyl or 2- or 3-furanyl, R$^1$ denotes H or CO$_2$R$^5$, (CH$_2$)$_n$COHet, CHO, (CH$_2$)$_n$OR$^5$, (CH$_2$)$_n$Het, (CH$_2$)$_n$N(R$^5$)$_2$, CH=N-OA, CH$_2$CH=N-OA, (CH$_2$)$_n$NHOA, (CH$_2$)$_n$(R$^5$)Het, (CH$_2$)$_n$CH=N-Het, (CH$_2$)$_n$OCOR', (CH$_2$)$_n$N(R$^5$)CH$_2$CH$_2$OR$^5$, (CH$_2$)$_n$N(R$^5$)CH$_2$CH$_2$OCF$_3$, (CH$_2$)$_n$N(R$^5$)C(R$^5$)OCOR$^5$, (CH$_2$)$_n$N(R')CH$_2$COHet, (CH$_2$)$_n$N(R$^5$)CH$_2$Het, (CH$_2$)$_n$N(R$^5$)CH$_2$CH$_2$Het, (CH$_2$)$_n$N(R$^5$)CH$_2$CH$_2$N(R')CH$_2$OCOR', (CH$_2$)$_n$N(R$^5$)CH$_2$CH$_2$N(R$^5$)$_2$, CH=CHCOOR$^5$, CH=CHCH$_2$NR$^5$Het, CH=CHCH$_2$N(R$^5$)$_2$, CH=CHCH$_2$OR$^5$ or (CH$_2$)$_n$N(R$^5$)Ar, R$^5$ denotes H or A A denotes straight-chain or branched alkyl or alkoxy having 1 to 10 C atoms, or alkenyl or alkenyloxyalkyl having 2 to 10 C atoms, Het is 1-piperidyl, 1-piperazyl, 1-(4-methyl)piperazyl, 1-(4-ethyl)piperazinyl, 1-(4-cyclopentyl)piperazinyl, 4-methylpiperazin-1-ylamine, 1-pyrrolidinyl, 1-pyrazolidinyl 1-(2-methyl)pyrazolidinyl, 1-imidazolidinyl or 1-(3-methyl)imidazolidinyl or 4-pyridyl, which is unsubstituted or substituted by one or more CN group, 2- or 4-pyridazyl, 2-, 4- or 5-pyrimidyl, 2- or 3-pyrazinyl, or a group of one of the formulae below

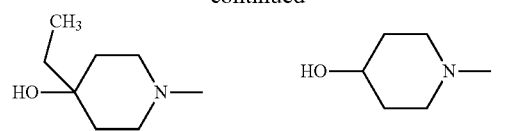
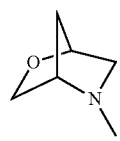
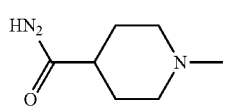
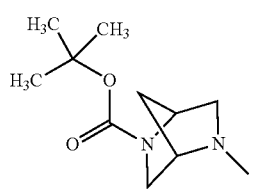
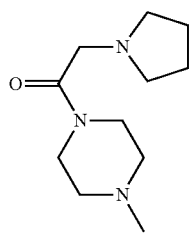
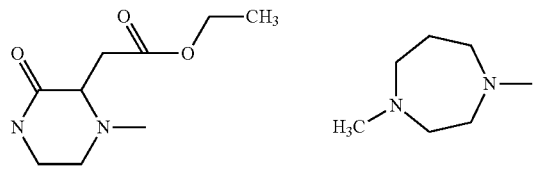
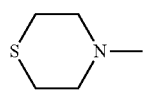
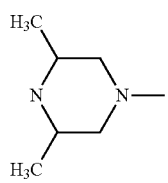
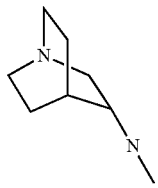
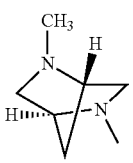
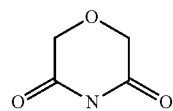
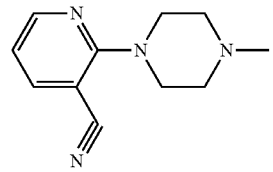
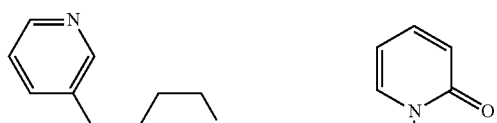
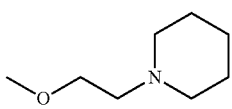
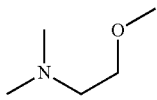
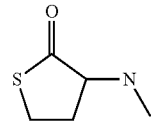
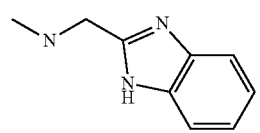
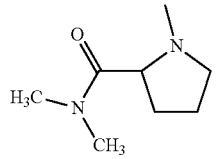
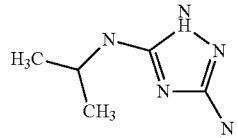
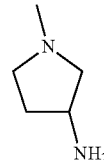
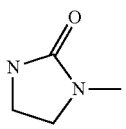
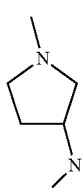
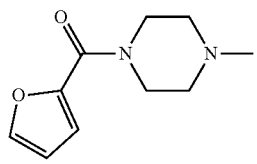
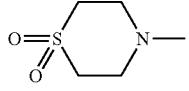
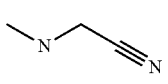
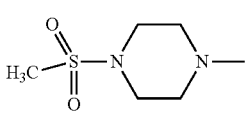

-continued

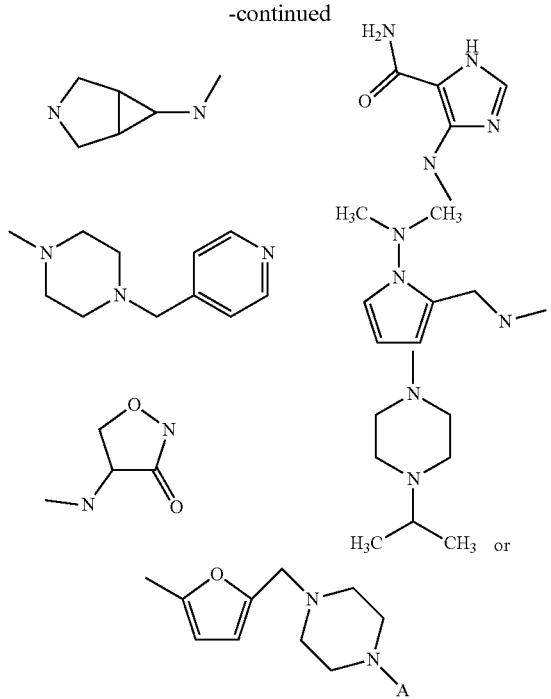

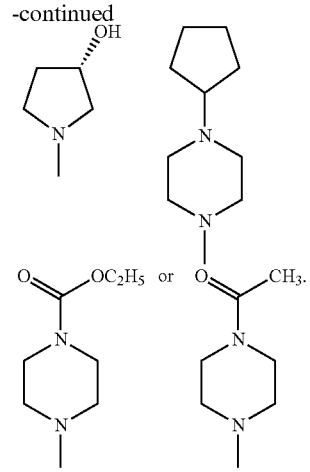

Ar denotes a phenyl radical which is unsubstituted or mono or polysubstituted by A and/or Hal, $OR^5$, $OOCR^5$, $COOR^5$, $CON(R^5)_2$, CN, $NO_2$, $NH_2$, $NHCOR^5$, $CF_3$ or $SO_2CH_3$, X denotes CH or N, n denotes 0, 1, 2, 3, 4 or 5 and Hal denotes F, Cl, Br or I, where, in the case that X has the meaning CH, $R^2$ and $R^4$ do not simultaneously denote H, or a salt, enantiomer, or racemate thereof, or a mixture of enantiomers, wherein at least one of the following three conditions I, II, or III is satisfied:

I) $R^4$ denotes H, Hal, CN, A or $NO_2$;

II) $R^2$ denotes H or alkyl;

III) Het is

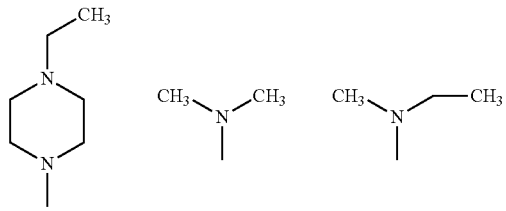

18. A compound according to claim 17, in which $R^4$ denotes H, Hal, CN, A or $NO_2$.

19. A compound according to claim 17, in which $R^2$ denotes H or alkyl.

20. A compound according to claim 17, in which Het is

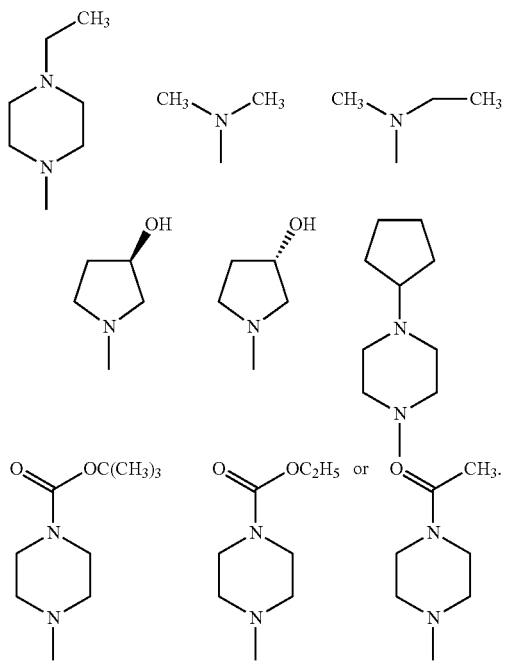

* * * * *